US007314973B2

(12) United States Patent
Smeekens et al.

(10) Patent No.: US 7,314,973 B2
(45) Date of Patent: Jan. 1, 2008

(54) PRODUCTION OF OLIGOSACCHARIDES IN TRANSGENIC PLANTS

(75) Inventors: Josephus Christianus Maria Smeekens, Driebergen (NL); Michaël Johannes Marcus Ebskamp, De Meern (NL); Hendrikus Andrianus Maria Geerts, Utrecht (NL); Petrus Jacobus Weisbeek, Den Dolder (NL)

(73) Assignee: Stichting Scheikundig Onderzoek In Nederland, The Hague (NL)

( * ) Notice: Subject to any disclaimer, the term of this patent is extended or adjusted under 35 U.S.C. 154(b) by 254 days.

(21) Appl. No.: 10/691,346

(22) Filed: Oct. 21, 2003

(65) Prior Publication Data

US 2004/0154052 A1 Aug. 5, 2004

Related U.S. Application Data

(63) Continuation of application No. 09/534,861, filed on Mar. 24, 2000, now abandoned, which is a continuation of application No. 09/019,385, filed on Feb. 5, 1998, now Pat. No. 6,147,280, which is a continuation of application No. 08/479,470, filed on Jun. 7, 1995, now abandoned.

(30) Foreign Application Priority Data

Aug. 7, 1994 (NL) .................................... 9401140
Apr. 5, 1995 (NL) .................................... 1000064

(51) Int. Cl.
*C12N 15/82* (2006.01)
*C12N 15/29* (2006.01)
*C12N 15/54* (2006.01)
*C12N 9/10* (2006.01)

(52) U.S. Cl. ...................... 800/284; 800/290; 435/193; 435/468; 435/440; 536/23.2; 536/23.6

(58) Field of Classification Search ..................... None
See application file for complete search history.

(56) References Cited

U.S. PATENT DOCUMENTS

| | | | |
|---|---|---|---|
| 4,801,540 | A | 1/1989 | Hiatt et al. |
| 4,927,811 | A | 5/1990 | Quarles |

FOREIGN PATENT DOCUMENTS

| | | | |
|---|---|---|---|
| AU | 9527878 | | 1/1996 |
| CA | 2076647 | | 8/1991 |
| CA | 22142308 | | 3/1994 |
| CA | 2171313 | | 3/1995 |
| DE | 42 27 061 | | 2/1994 |
| DE | 43 30 960 | | 3/1995 |
| DE | 44 20 223 | | 5/1995 |
| EP | 0 133 547 | | 2/1985 |
| EP | 0 474 046 | | 3/1992 |
| GB | 2072679 | | 10/1981 |
| JP | 56 154967 | A | 11/1981 |
| JP | A-58201980 | | 11/1983 |
| JP | A-02163093 | | 6/1990 |
| JP | 05504568 | | 7/1993 |
| WO | WO89/12386 | | 12/1989 |
| WO | 91/13076 | A1 | 9/1991 |
| WO | WO91/13076 | | 9/1991 |
| WO | 93/02196 | A1 | 2/1993 |
| WO | WO93/07159 | | 4/1993 |
| WO | WO94/04692 | | 3/1994 |
| WO | WO94/14970 | | 7/1994 |
| WO | WO94/27617 | | 12/1994 |
| WO | WO 95/13389 | | 5/1995 |
| WO | WO95/13389 | * | 5/1995 |
| WO | 96/21023 | A1 | 7/1996 |

OTHER PUBLICATIONS

Vergauwen et al Plant Physiology 2003, 133:391-401.*
Ritsema et al 2004 Plant Molecular Biology 54:853-863.*
Turk et al 1997 New Phytology 136:29-38.*
Bancal, P., et al., "Fructan Chemical Structure and Sensitivity to an Exohydrolase," *Carbohydrate Research 217*:137-151, 1991.
"Bifidus Growth-Stimulating Substances," *Chemical Abstracts 100*(17):137377, Apr. 23, 1994.
Chatterton, N.J., et al., "Structure of Fructan Oligomers in Orchardgrass (*Dactylis glomerata* L.)," *J. Plant Physiology 142*:552-556, 1993.
Cote, G.L., et al., "Purification and Properties of an Extracellular Levansucrase from *Erwinia herbicola* NRRL B-1678," *Carbohydrate Research 190*:299-307, 1989.
Ebskamp, M.J.M., et al., "Accumulation of Fructose Polymers in Transgenic Tobacco," *Bio/Technology 12*:272-275, Mar. 1994.
Fuchs, A., "Current and Potential Food and Non-Food Applications of Fructans," *Redesigning Crop Products for Biotechnology 19*:555-560, 1991.
Geier, G., et al, "Levansucrase as a Virulence Factor in the Etiology of Fireblight," in W. Zeller (ed.), *Communications from the Federal Biological Institute for Agricultural and Forestry Berlin-Dahlem*, Symposium on Fireblight, Ladenburg, Germany (Jun. 13-14, 1991), 1992, pp. 78-81. Translation provided.

(Continued)

*Primary Examiner*—Russell P. Kallis
*Assistant Examiner*—Brent T Page
(74) *Attorney, Agent, or Firm*—Christensen O'Connor Johnson Kindness PLLC

(57) ABSTRACT

The invention relates to a method for producing oligosaccharides, comprising selecting a gene which codes for an enzyme which is capable of converting sucrose into an oligosaccharide; linking the gene to suitable transcription-initiation and transcription-termination signals in order to provide an expression construct; transforming a suitable plant cell with the expression construct; regenerating a transgenic plant from the transformed plant cell; culturing the transgenic plant under conditions enabling the expression and activity of the enzyme; and isolating the oligosaccharides from the transgenic plant. The invention further relates to the product obtained by means of the method and to the use thereof, in addition to transgenic plants and parts thereof which are capable of producing oligosaccharides.

4 Claims, 15 Drawing Sheets

OTHER PUBLICATIONS

Hirayama, M., et al., "Production and Characteristics of Fructo-oligosaccharides," *Chemical Abstracts 120*(5):52935, Jan. 31, 1994.

John, P., "Fructan Quality and Fructan Synthesis," *Biochemical Society Transactions 19*(3):569-572, 1991.

"Microbe belonging to Scopulariopsis generates kestose by culturing microbe in medium containing sucrose and decomposes glucose as by-product," JP-A-2163093, Jun. 22, 1990. (WPI Database Abstract #9235349.).

Nakano, Y.J., et al., "Mechanism of Streptococcus Mutans Glucosyltransferases: Hybrid-Enzyme Analysis," *Journal of Bacteriology 174*(17):5639-5646, Sep. 1992.

Rastall, R.A., et al. "Synthesis of Oligosaccharides by Reversal of a Fungal B-Glucanase," *Biotechnology Letters 14*(5):373-378, May 19, 1992.

Roberfroid, M., "Dietary Fiber, Inulin, and Oligofructose: A Review Comparing Their Physiological Effects," *Crit. Rev. Food Sci. Nutr. 33*(2):103-148, 1993. (Medline Database Abstract #93236728.).

Shiroza, T., et al., "Sequence Analysis of the *Streptococcus mutans* Fructosyltransferase Gene and Flanking Regions," *Journal of Bacteriology 170*(2):810-816, Feb. 1988.

Simmen, U., et al., "Fructan Synthesis in Excised Barley Leaves," *Plant Physiology 101*(2):459-468, Feb. 1993.

Smeekens, S., et al., "Molecular biology of fructan accumulation in plants," *Biochemical Society Transactions 19*(3):565-569, 1991.

Steinmetz, M., et al., "The DNA Sequence of the Gene for the Secreted *Bacillus Subtillis* Enzyme Levansucrase and Its Genetic Control Sites," *Mol. Gen. Genet. 200*:20-228 (Springer-Verlag 1985).

Van Der Meer, I.M., et al., "Fructan as a New Carbohydrate Sink in Transgenic Potato Plants," *The Plant Cell 6*:561-570, Apr. 1994.

Vijn, I., et al., Fructan of the inulin neoseries is synthesized in transgenic chicory plants (*Cichorium intybus* L.) harbouring onion (*Allium cepa* L.) Fructan:Fructan 6G-Fructosyltransferase, *Plant J. 11*(7):387-398, 1997.

Yamamoto, S., et al., "The Mode of Synthesis of Levan by Bacillus Subtilis Levansucrase," *Agricultural and Biological Chemistry 49*(2):343-349, Feb. 1985.

Hirayama, M., et al., "Production and Characteristics of Fructo-Oligosaccharides, " Chemical Abstracts 120:841, 1994.

Luscher, M., et al., "Purification and Characterization on Fructan: Fructan Fructosyltransferase From Jerusalem Artichoke (Helianthus tuberosus L.), " New Phytology 123:717-724, 1993.

Oakes, J.V., et al., "Production of Cyclodextrins, a Novel Carbohydrate, in the Tubers of Transgenic Potato Plants, " Bio/Technology 9:982-986, Oct. 1991.

Tokunaga, T., et al., "Influence of Chronic Intake of New Sweetener Frutooligosaccharide (Neosugar) on Growth and Gastrointestinal Function of the Rat, " Journal of Nutritional Science and Vitaminology 32:111-121, 1986.

Oku, T., "Caloric Evaluation of Reduced-Energy Bulking Sweeteners, " in D.R. Romsos et al., (eds.), Obesity: Dietary Factors and Control, Japan Scientific Societies Press, Tokyo, 1991, pp. 169-180.

* cited by examiner

SDS - PAGE OF SST FROM ONION SEED

Fig. 11B

| | | 86 115 | 125 132 | 157 164 | 220 229 | 280 290 | 343 353 |
|---|---|---|---|---|---|---|---|
| H.v. | 6sft | HFQtaKNY.MsDPNGLMY..YrGWYHmFYQYNP | MeWGHAVS | ..lSGSmTVL | DFRDPmTAWy | eWECiDFyPVg | DwGK.FYAStsF |
| V.r. | Inv | HFQPEKNW.MNDPNGPMY..YKGWYHfFYQYNP | IVWGHAVS | ..WtGSATIL | DFRDPTTAWl | MWECvDFFPVS | DYGi.FYASktF |
| D.c. | Inv | HFQPnqNW.MNDPNGPlf..YKGWYHLFYQYNP | IVWGHAVS | ..WtGSATIL | DFRDPTTAWr | MWECvDFyPVS | DYGi.YYASktF |
| L.e. | Inv | HFQPgKNW.MNDPNGPlY..hKGWYHLFYQYNP | ItWGHAVS | ..WtGSATIL | DFRDPTTAWt | MWECvDFyPVS | DYGk.YYASktF |
| D.c. | cwInv | HFQPkgNW.iNDPNGPMY..YKGvYHLFYQYNP | IVWaHsVS | ..rSGSATIL | aFRDPTTAWl | MWECPDFFPVS | DYGn.FYASktF |
| A.s. | Inv | ............NGPMY..YNGiYHssYQYNP | IVWGHAVS | ..WtGSATIL | qFRDPTTgWI | ........... | ............ |
| E.c. | Inv | HLaPpaGW.MNDPNGLiY..FNGrYHaFFQhhp | MhWGHats | ..FSGSA.VD | hFRDPK...v | MWECPDFFrc. | DYGhDFYApQsm |
| S.m. | Scrb | HiePktGl.LNDPNGfsY..FNGkfnLFYQnwp | ksWiHteS | ..ySGSA.ye | hFRDPq...I | MiECPnLvfI. | DfGfecYAtQaf |

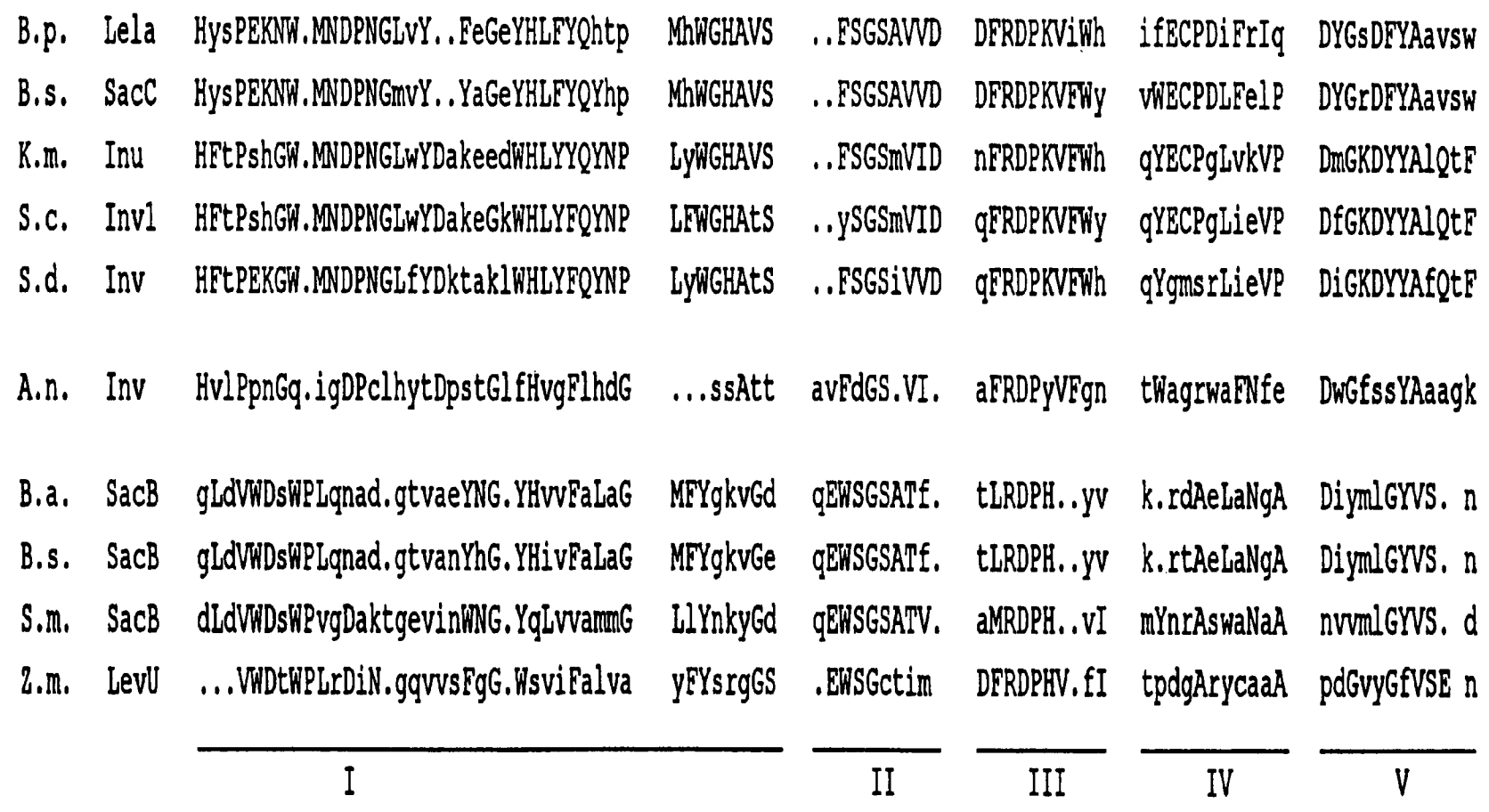

| | | | | | | | |
|---|---|---|---|---|---|---|---|
| B.p. | Lela | HysPEKNW.MNDPNGLvY..FeGeYHLFYQhtp | MhWGHAVS | ..FSGSAVVD | DFRDPKViWh | ifECPDiFrIq | DYGsDFYAavsw |
| B.s. | SacC | HysPEKNW.MNDPNGmvY..YaGeYHLFYQYhp | MhWGHAVS | ..FSGSAVVD | DFRDPKVFWy | vWECPDLFelP | DYGrDFYAavsw |
| K.m. | Inu | HFtPshGW.MNDPNGLwYDakeedWHLYYQYNP | LyWGHAVS | ..FSGSmVID | nFRDPKVFWh | qYECPgLvkVP | DmGKDYYAlQtF |
| S.c. | Inv1 | HFtPshGW.MNDPNGLwYDakeGkWHLYFQYNP | LFWGHAtS | ..ySGSmVID | qFRDPKVFWy | qYECPgLieVP | DfGKDYYAlQtF |
| S.d. | Inv | HFtPEKGW.MNDPNGLfYDktaklWHLYFQYNP | LyWGHAtS | ..FSGSiVVD | qFRDPKVFWh | qYgmsrLieVP | DiGKDYYAfQtF |
| A.n. | Inv | HvlPpnGq.igDPclhytDpstGlfHvgFlhdG | ...ssAtt | avFdGS.VI. | aFRDPyVFgn | tWagrwaFNfe | DwGfssYAaagk |
| B.a. | SacB | gLdVWDsWPLqnad.gtvaeYNG.YHvvFaLaG | MFYgkvGd | qEWSGSATf. | tLRDPH..yv | k.rdAeLaNgA | DiymlGYVS. n |
| B.s. | SacB | gLdVWDsWPLqnad.gtvanYhG.YHivFaLaG | MFYgkvGe | qEWSGSATf. | tLRDPH..yv | k.rtAeLaNgA | DiymlGYVS. n |
| S.m. | SacB | dLdVWDsWPvgDaktgevinWNG.YqLvvammG | LlYnkyGd | qEWSGSATV. | aMRDPH..vI | mYnrAswaNaA | nvvmlGYVS. d |
| Z.m. | LevU | ...VWDtWPLrDiN.gqvvsFgG.WsviFalva | yFYsrgGS | .EWSGctim | DFRDPHV.fI | tpdgArycaaA | pdGvyGfVSE n |
| | | I | | II | III | IV | V |

Fig. 11C

IEF (Helianthus tuberosus FFT)

PRODUCTION OF OLIGOSACCHARIDES IN TRANSGENIC PLANTS

CROSS-REFERENCE TO RELATED APPLICATIONS

This application is a continuation of application Ser. No. 09/534,861, filed March 24, 2000, now abandoned which is a continuation of application Ser. No. 09/019,385, filed Feb. 5, 1998, now U.S. Pat. No. 6,147,280, which is a continuation of application Ser. No. 08/479,470, filed Jun. 7, 1995, now abandoned.

FIELD OF THE INVENTION

The present invention relates to a method for producing oligosaccharides, to the oligosaccharides produced in this manner, to transgenic plants and plant cells capable of producing oligosaccharides and to the applications of the oligosaccharides obtained in this manner.

BACKGROUND OF THE INVENTION

In the food industry a growing trend toward "light" and low calorie can be observed. The use of too much fat and/or sugar in products is avoided. To nevertheless be able to provide food products with a sweet taste, an increasing number of sugar substitutes are becoming commercially available. Aspartame is a known example thereof. Aspartame, however, has poor organoleptic properties.

Another type of sugar substitute is formed by oligosaccharides. Oligosaccharides are molecules which consist of two or more monosaccharides such as fructose and/or glucose. The monosaccharides in oligosaccharides are linked to each other either by β-(2-1) or by β-(2-6) bonds. The number of monosaccharides in an oligosaccharide is indicated by means of the DP-value ("Degree of Polymerisation"). A DP-value of 3 means that the oligosaccharide is composed of three monosaccharides. Oligofructoses are oligosaccharides consisting entirely of fructose units. When an oligosaccharide also comprises one or more glucose units these will be linked by means of an α-(1-2) bond to a fructose unit. The composition of oligosaccharides is also designated with the formula $G_mF_n$, wherein G represents glucose and F fructose and wherein m equals 0 or 1 and n is an integer larger than or equal to 0. Particularly suitable oligosaccharides are those wherein m equals 1 and n is 2 to 8, preferably 2 or 3.

Oligosaccharides can hardly be hydrolysed, if at all, in the human stomach and small intestine. It is known of oligofructose that the digestive enzymes of the human have no effect on the β-(2-1) and β-(2-6) bond in the molecule. They therefore pass through the stomach and the small intestine without being degraded and absorbed into the body. The oligosaccharides do not however leave the body but are metabolised by the microbial flora of the large intestine. Released herein in addition to gas are volatile fatty acids which in turn again serve as an energy source for the intestinal flora. This phenomenon explains why oligosaccharides have a lower energy value for humans than free sugars such as glucose, fructose and sucrose, which are absorbed into the body. Oligosaccharides do however have sufficient sweetening power to serve as sugar substitutes.

It is further known that oligosaccharides, particularly oligofructose, have a bifidogenic effect, that is, that they stimulate the growth of Bifidobacteria in the digestive tract. Bifidobacteria protect against the development of pathogenic bacteria and thereby have a positive influence on health. In addition, oligosaccharides are nutritional fibres.

Different oligosaccharides, which are prepared in diverse ways, are already commercially available.

Oligosaccharides can be made by partial enzymatic hydrolysis of longer vegetable inulin chains. A method herefor is described for instance in European patent application 440.074.

Oligosaccharides can likewise be enzymatically synthesized. For this enzymatic production route use is made of enzymes, fructosyltransferases, which convert sucrose to a mixture of oligosaccharides and which are isolated from different micro-organisms (see Japanese Patent 80/40193).

The known production routes have a number of drawbacks however. Firstly, the known production methods are relatively expensive. In addition to the desired oligosaccharides with a chain length of 2 to about 7, in the produced mixture there also occur a comparatively large number of free sugars and oligosaccharides with a higher chain length. The drawback to many free sugars is that they result in an increase in the energy value of the mixture. Free sugars have for instance an energy content of 17 kilojoule per gram, while pure $GF_2$ and $GF_3$ have an energy content of 4 to 6 kilojoule per gram. In addition, free sugars cause dental decay (caries).

Conversely, oligosaccharides with too high a chain length have too little sweetening power, which causes the average sweetening power of the mixture to fall.

In contrast to some other sweeteners, such as for example Aspartame, oligosaccharides have good organoleptic properties.

It is the object of the present invention to provide an alternative production route for oligosaccharides with which the above stated drawbacks are avoided.

SUMMARY OF THE INVENTION

To this end the invention provides a method for producing oligosaccharides, comprising the steps of:

a) selecting a gene which codes for an enzyme capable of converting sucrose into an oligosaccharide;

b) linking the gene to suitable transcription-initiation and transcription-termination signals in order to provide an expression construct;

c) transforming a suitable plant cell with the expression construct;

d) regenerating a transgenic plant from the transformed plant cell;

e) culturing the transgenic plant under conditions enabling the expression and activity of the enzyme; and f) isolating the oligosaccharides from the transgenic plant.

The invention therefore provides a method with which by means of transgenic plants or plant cells an oligosaccharide or a mixture of oligosaccharides can be produced which have more desirable properties compared with the oligosaccharides prepared by known industrial processes.

The particular advantage of the method according to the invention is that the chain length distribution is narrower, whereby no or few free sugars occur in the end product. The consequence hereof is a lower cariogenicity and the desired lower energy value. There also occur fewer oligosaccharides with a chain length of more than 5. The advantage hereof is that the oligosaccharides produced according to the invention have a higher specific sweetening capacity. It is the case that the sweetening capacity depends on the "average chain length". The higher the average chain length of a mixture, the lower the sweetening capacity. The advantage of a high specific sweetening capacity is that extra sweeteners hardly have to be added in processing of the product.

A similar consideration applies to solubility. It is also the case here that when the average chain length increases the solubility decreases. The mixtures according to the present invention have a higher solubility than mixtures obtained by means of enzymatic synthesis or enzymatic hydrolysis. In addition, production costs are considerably reduced.

There are indications that short chains can be absorbed better in the bacteria body of Bifidus than long ones. The oligosaccharide mixtures produced by means of the method according to the invention will therefore have a higher bifidogenic effect.

BRIEF DESCRIPTION OF THE DRAWINGS

FIGS. 11B and 11C show the amino acid sequence of 6-SFT from barley compared to different invertases, levanases and levansucrases.

DETAILED DESCRIPTION OF THE PREFERRED EMBODIMENT

Figure 1:
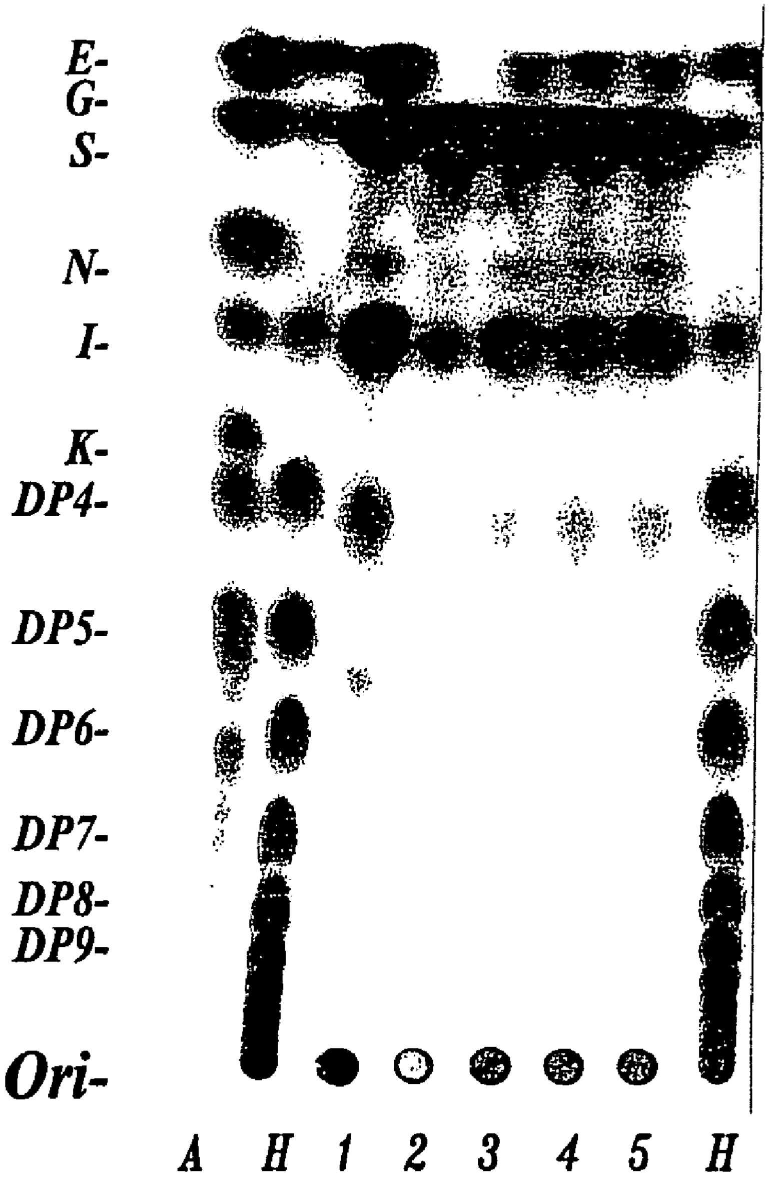
FIG. 1 is a photograph illustrating the oligosaccharide-producing activity of wild type and modified forms of the *Streptococcus mutans* fructocyltransferase incubated with sucrose and analyzed on TLC.

In order to select a gene which codes for an enzyme capable of converting sucrose into an oligosaccharide it is possible to search in any possible organism which contains fructosyltransferase activity, for instance micro-organisms such as bacteria, or plants. It is known of many micro-organisms that they contain fructosyltransferases which are capable of producing fructans from sucrose. These enzymes transfer fructose units from sucrose to a fructan acceptor molecule. Microbial fructosyltransferases normally produce fructans with a high DP. The use of a number of fructosyltransferases to manufacture transgenic plants for the production of such polysaccharides is already described in the literature. It is thus known that by incorporating the SacB-gene of *Bacillus subtilis* in plants the fructan pattern of these plants can be modified (see International Publication No. WO 89/12386). This still relates however to the production of high-molecular polysaccharides.

Another gene which is known to code for a fructosyltransferase which can convert sucrose into high-molecular fructans is the ftf gene of *Streptococcus mutans*. According to the present invention. It has now been found surprisingly that in addition to high-molecular weight fructans this fructosyltransferase also produces significant quantities of oligosaccharides in the trisaccharide class (1-kestose). Mutants have also been found which only accumulate trisaccharides and not polysaccharides.

Further known are mutants of the SacB gene of *Bacillus subtilis* which likewise produce mainly trisaccharides.

A large number of other micro-organisms is likewise capable of fructosyltransferase production. These comprise, but are not limited to, endospore-forming rod bacteria and cocci (for example *Bacillus*) gram-positive cocci (for instance *Streptococcus*), gram-negative aerobic rod bacteria and cocci (for instance *Pseudomonas, Xanthomonas, Azotobacter*) gram-negative facultative anaerobic rod bacteria (for instance *Erwinia, Zymomonas*), actinomycetes (for instance *Actinomyces, Rothia*) and cyanobacteria (for instance *Tolypothrix tenuis*).

The genes which code for these fructosyltransferases can optionally be modified by targeted or random mutagenesis techniques in order to provide enzymes possessing the desired oligosaccharide-synthesizing enzymatic properties.

Bacterial fructosyltransferases have a relatively low KM for sucrose, approximately 20 mM. The sucrose concentrations in most plants is considerably higher and these enzymes will therefore also be active in plants. An important property of bacterial fructosyltransferase is their activity at low temperatures to 0° C. Plants often come into contact with these temperatures but the bacterial enzymes will still be active even under these conditions.

Fructosyltransferases can also be of vegetable origin. In plants the biosynthesis and degradation of fructan only occur in a limited number of species. Examples are the Asteraceae, Liliaceae and Poaceae families. Starting from the known vegetable fructosyltransferases, the genes suitable for the present invention can be isolated or manufactured either by targeted or random mutagenesis or by selection of already naturally occurring mutants.

An example of a very suitable vegetable fructosyltransferase is the sucrose-sucrose-fructosyltransferase (SST) which occurs in different plant species and which in particular catalyses the synthesis of trisaccharides.

Another example is the sucrose-fructan-6-fructosyltransferase (6-SFT) from barley (*Hordeum vulgare* L.). According to one embodiment of the invention, transgenic plants are provided which express 6-SFT for the production of oligo-saccharides.

According to another embodiment of the invention, transgenic plants are also provided which contain the fructan-fructan-fructosyltransferase (FFT) of the Jerusalem artichoke (*Helianthus tuberosus* L.).

For expression in plants of the selected fructosyltransferase gene, transcription-initiation signals such as promotors, enhancers and the like can be added to the gene to obtain the desired expression construct. Such expression promotors can be specific to a special cell type or can be active in a wide diversity of cell types. In addition, the time and site of expression can be determined by use of for instance development-specific promotors. A generally used promotor for gene expression in plants is the 35S Cauliflower Mosaic Virus Promotor (CaMV promoter) which is active in many cell types in the plant depending on the stage of development of the plant. When the fructosyltransferase gene originates from a plant it is also possible to use its own regulatory sequences.

The preferred promotor can be a tissue-specific or constitutive promotor, strong or weak, depending on target plant and purpose. Examples of suitable promoters are the "sink"-specific patatine promotor and the granule-bound starch synthase promotor of the potato, or the sporamine promotor of the sweet potato.

To further increase transcription levels the promotor can be modified and contain an enhancer duplication.

The translation of the mRNAs can be improved by adding a translational enhancer, such as the Alfalfa Mosaic Virus RNA4 translation enhancer signal, which must be present in the transcribed 5' non-translated region.

For correct termination of transcription a terminator sequence can be added to the constructs. An example of such a sequence is the nopaline synthase gene termination sequence.

The choice of expression signals suitable for a specific situation lies of course within the reach of the average skilled person without further inventive work having to be performed for this purpose.

Sucrose, the substrate for the fructosyltransferases, is a carbohydrate present at many different locations. It is synthesized in the cytoplasm and significant quantities can also be found in cytosol, vacuole and the extracellular space (the apoplast) or other possible locations.

Since biochemical processes in plant cells are likewise often limited to a single or a number of cellular compartments, it is desirable to cause the accumulation of the products of the newly introduced genes to take place in a specific compartment. For this purpose targeting sequences which are specific to cellular compartments can be present in the expression construct close to the coding part of the fructosyltransferase genes which are expressed in the transgenic plants. Specific amino acid regions for the targeting to the different cellular locations have already been identified and analysed. These DNA-sequences can be linked to the fructosyltransferase genes such that the enzymatic activity is directed to a desired compartment of the cell or the plant.

In a preferred embodiment of the invention the expression construct therefore also comprises a targeting sequence for directing the fructosyltransferase activity to one or more specific plant cell compartments. Examples of targeting sequences are the signal sequence and vacuolar targeting sequence of the carboxypeptidase Y (cpy) gene, that of patatine from the potato, that of sporamine from the sweet potato, or the signal sequence and apoplastic targeting sequence of the pathogenesis-related protein S-gene (pr-s). These are examples, and the skilled person will be capable of selecting other targeting sequences.

The expression construct can in principle be modified such that targeting takes place to any random cell compartment, such as the vacuole, plastides, cell wall, cytoplasm etc.

It is often advantageous for the plant to control not only the location but also the time of expression of the introduced genes. It is for instance normally desired to limit the expression of the newly introduced enzymatic activities to specific parts of the plant, for instance harvestable organs such as tubers, fruits or seeds. It is moreover often desired to initiate expression in these organs at a particular stage of development. This is certainly the case when the expression of the introduced genes interferes with normal development of such organs.

The oligosaccharides according to the invention can be used as substitutes for sugar, glucose syrup and isoglucose in "light" versions of different food products. Examples of such food products are confectionery, biscuits, cakes, dairy products, baby food, ice cream and other desserts, chocolate and the like. The stimulation of Bifidobacteria is also important for the health of animals. The oligosaccharides according to the invention can therefore also be applied in for instance animal feed.

The present invention will be further elucidated on the basis of the examples hereinbelow, which are only given by way of illustration of the invention and are not intended to limit the invention in any way. Reference is made in the examples to the annexed figures which show the following:

FIG. 1 shows the oligosaccharide-producing activity of wildtype and modified forms of the *Streptococcus mutans* fructosyltransferase (ftf) which is incubated with sucrose and analysed on TLC as described by Cairns, A. J. and Pollock, C. J., New Phytol. 109, 399-405 (1988). Samples of cultures which were derived from colonies and purified proteins were incubated overnight with 200 mM sucrose in 50 mM sodium phosphate buffer with 1% Triton X-100 at 37° C. Lane 1 shows the reaction products of an *S. mutans* culture; lane 2 shows the activity of the purified enzyme from *S. mutans*; lane 3 shows the activity of an *E. coli* strain harbouring the plasmid pTS102; lane 4 shows the activity of an *E. coli* strain harbouring plasmid pTD2; and lane 5 shows the activity of an *E. coli* cell which is transformed with the mature *S. mutans* fructosyltransferase gene under the regulation of an *E. coli* promotor. The oligosaccharide standards used are in lane A, an extract of an *Allium cepa* bulb, and in lane H, an extract of a *Helianthus tuberosus* tuber. In the figure, F represents fructose, G represents glucose, S represents sucrose (disaccharide), N represents neokestose (F2-6G1-2F, trisaccharide), I represents 1-kestose (G1-2F1-2F, trisaccharide), and K represents kestose (G1-2F6-2F, trisaccharide). Higher oligosaccharides (DP=4-9) are likewise indicated.

Figure 2:
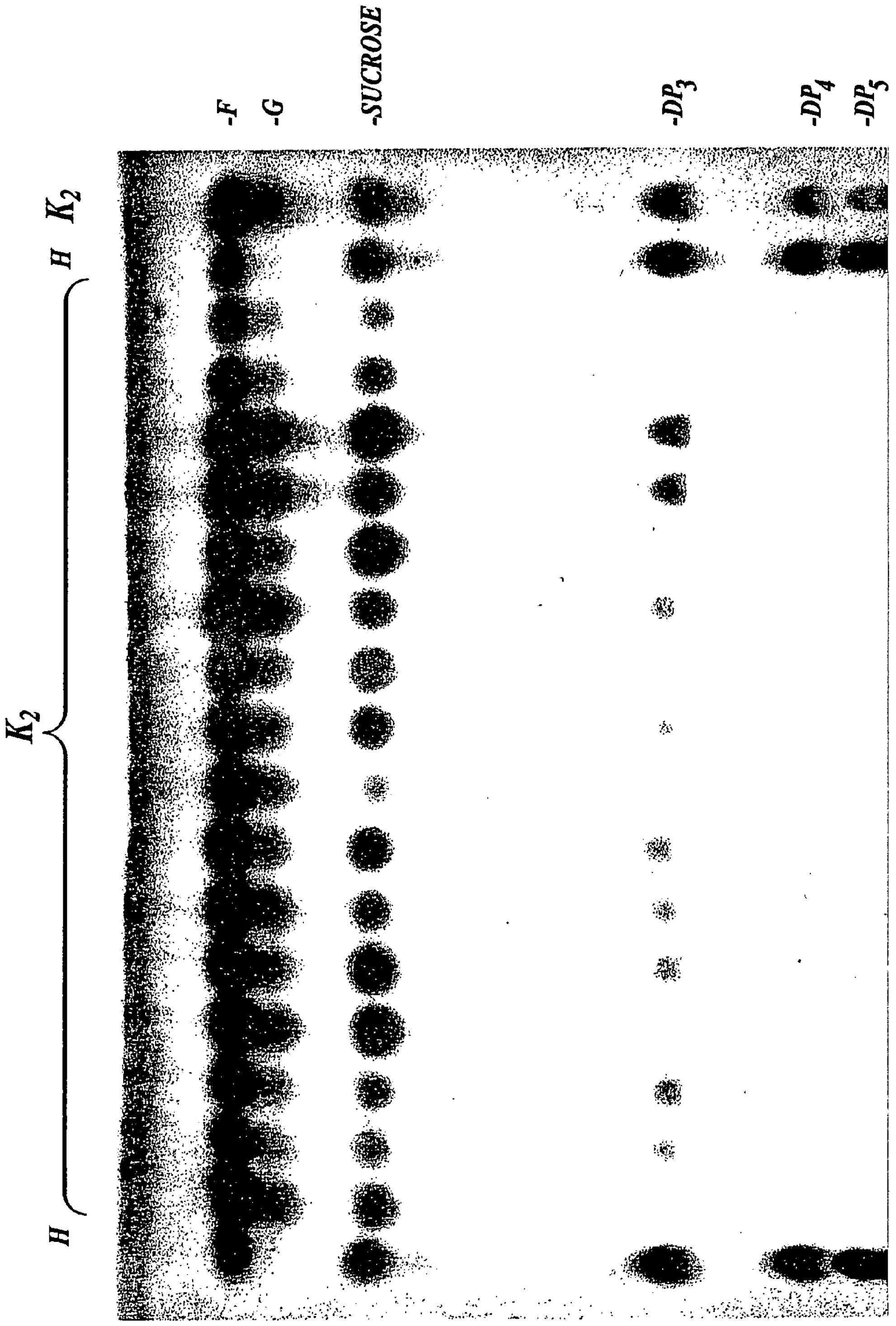
FIG. 2 is a photograph illustrating the results of TLC-analysis of transgenic tobacco plants which express the fructocyltransferase gene of *Streptococcus mutans.*

FIG. 2 shows the TLC-analysis of transgenic tobacco plants (KZ) which express the fructosyltransferase gene of *S. mutans*. Oligosaccharides accumulate in these plants. Lane H shows, as a control, an extract of a *Helianthus tuberosus* tuber.

Figure 3:
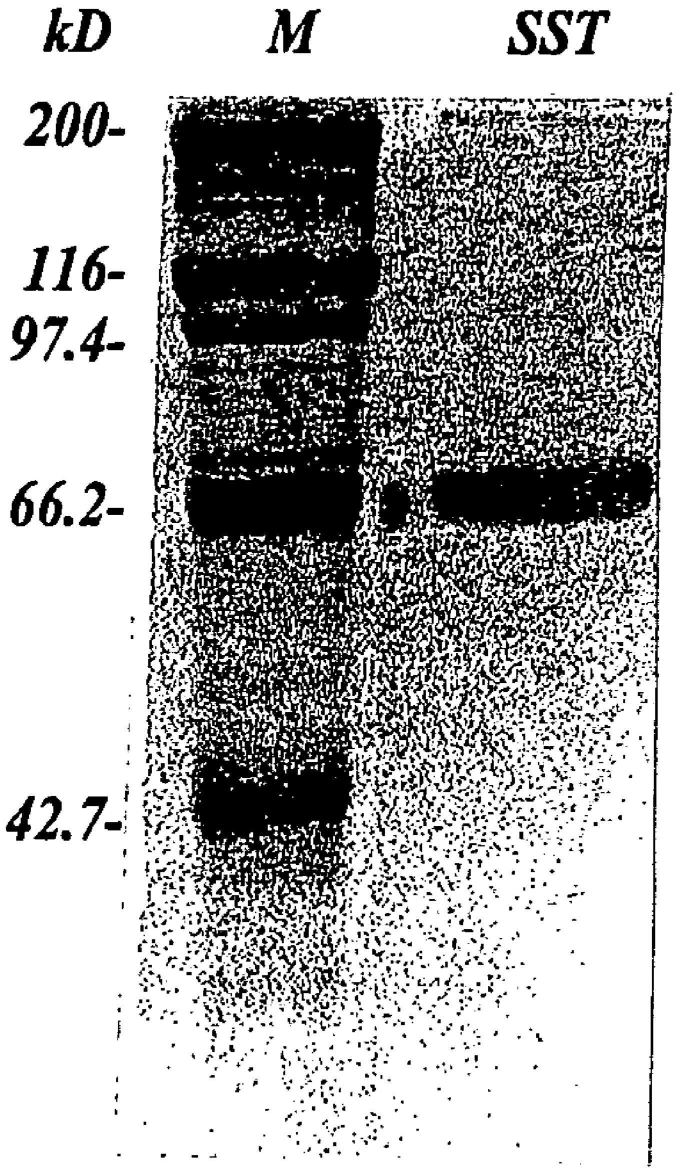
FIG. 3 is a photograph illustrating the SDS-PAGE gel of purified SST from onion seed.

FIG. 3 shows the SDS-PAGE gel of purified SST from onion seed. A single band was visible in the SST sample on this gel, stained by means of silver-staining. M represents molecular weight markers wherein their size is indicated in kilodaltons (kD).

Figure 4:
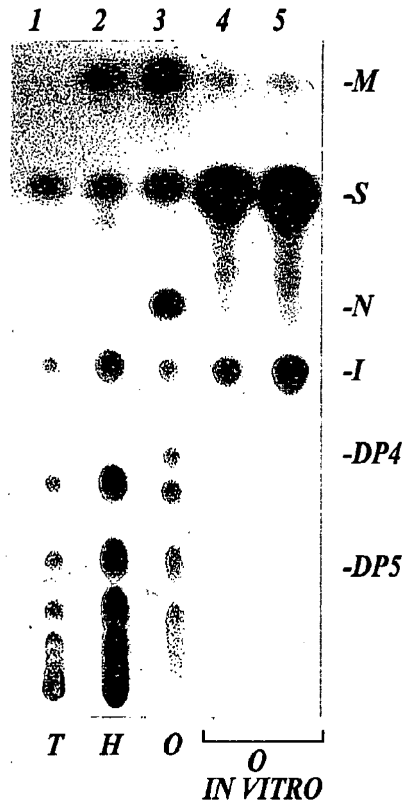
FIG. 4 is a photograph illustrating the results of TLC-analysis of the reaction products of purified SST from onion seed incubated with sucrose.

FIG. 4 shows the reaction products of purified SST from onion seed which is incubated with sucrose (lanes 4 and 5: O-in vitro). Only trisaccharides are formed. Lane 1 shows the extract of tulip stalks (T), lane 2 shows the extract of *Helianthus tuberosus* tubers (H), and lane 3 shows the extract of an *Allium cepa* bulb (O). M represents monosaccharide, S represents sucrose (disaccharide), N represents neokestose (F2-6G1-2F, trisaccharide), and I represents 1-kestose (G1-2F1-2P, trisaccharide). Higher oligosaccharides (DP4-5) are likewise indicated. The products were analysed on TLC as described for FIG. 1.

Figure 5:
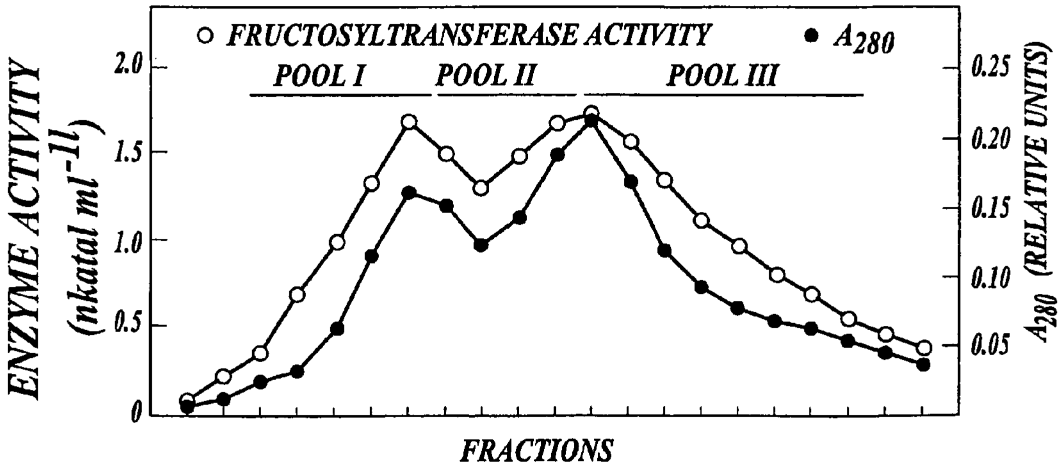
FIG. 5 is a graph of the protein elution profile (A280) and the fructocyltransferase activity of two iso forms of 6-SFT obtained from barley.
Figure 6A:
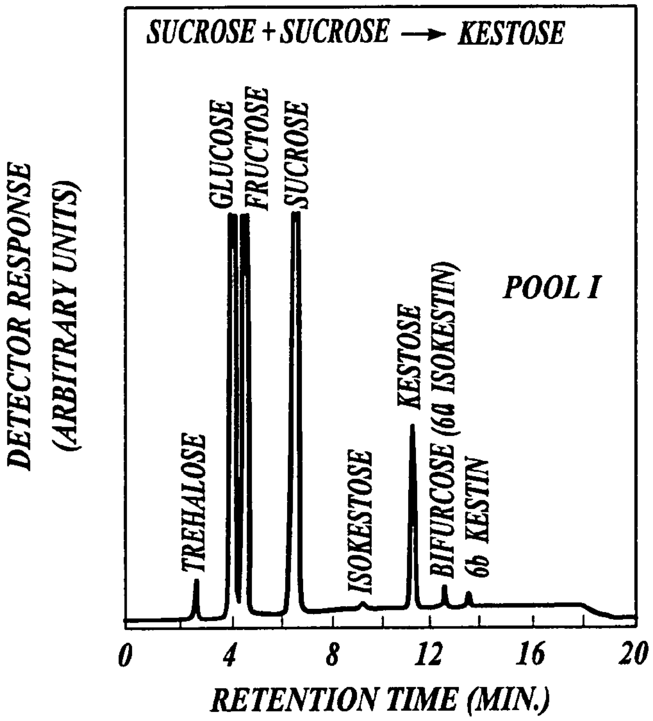
FIGS. 6A through 6D are chromatograms of 2 isoforms of 6-SFT obtained from barley.
Figure 6B:
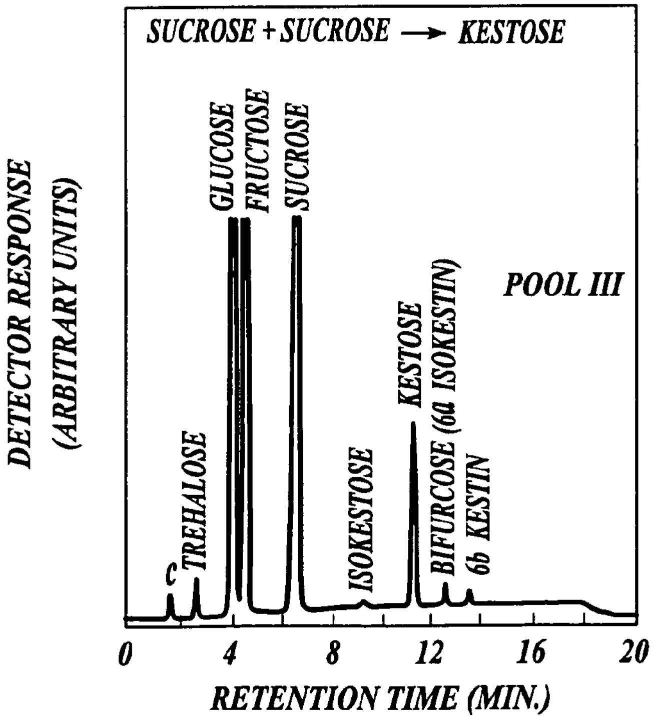
Figure 6C:
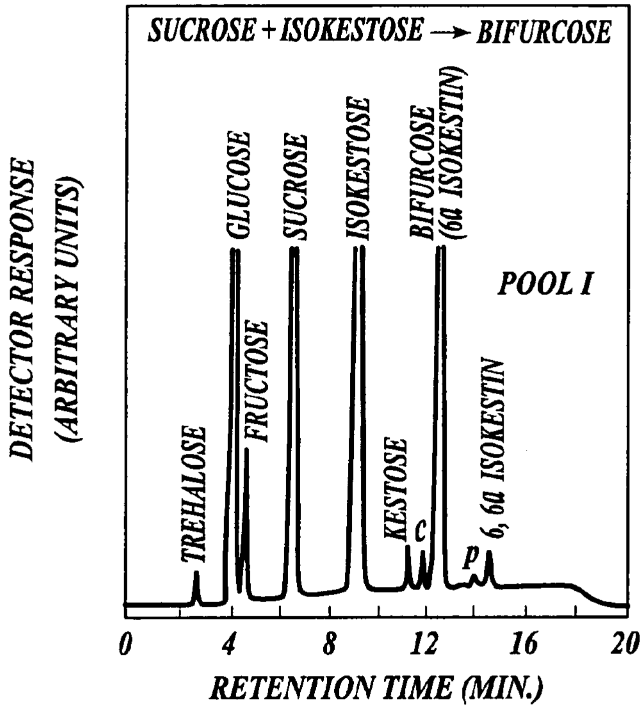
Figure 6D:
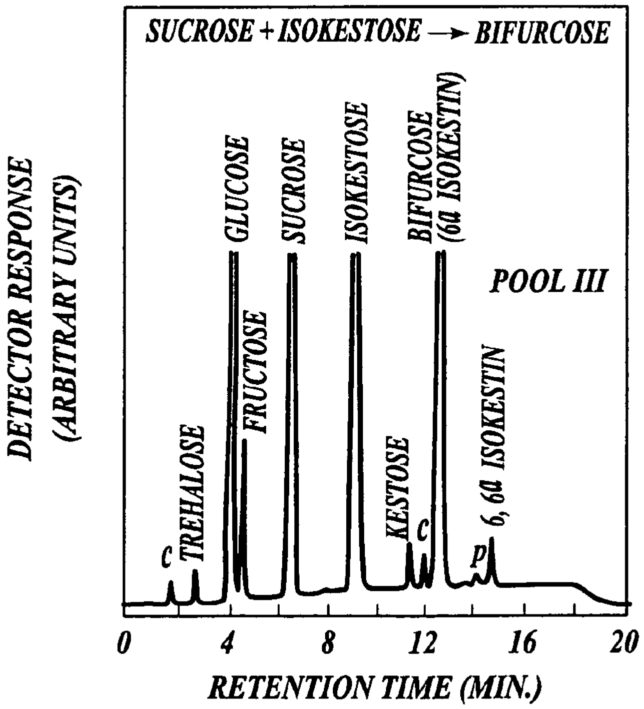

FIGS. 5 and 6A through 6D show the separation of 2 isoforms of the sucrose-fructan 6-fructosyltransferase (6-SFT) from barley after the second anion exchange chromatography step on a Resource Q column in a purification procedure. FIG. 5 shows the protein elution profile (A280) and the fructosyltransferase activity of the fractions obtained after chromatography after incubation with 0.2M sucrose in 25 mM methylpiperazine (HCl) buffer (pH 5.75). The chromatograms (FIGS. 6A through 6D were obtained by pulsed amperometric detection after anion exchange HPLC separation on a CarboPack-PA100 column. The reaction products were obtained after incubation of pool I and pool III with sucrose alone, or sucrose and isokestose. The carbohydrates were identified by their retention times and trehalose was used as an internal standard.

Open circles in FIG. 5 represent fructosyltransferase activity, which is indicated as the sum of formed kestose, bifurcose, isokestine and kestine. In FIGS. 6A through 6D, p corresponds with a non-identified product resulting from isokestose contaminants, and c with a contamination of the isokestose substrate.

Figure 7:
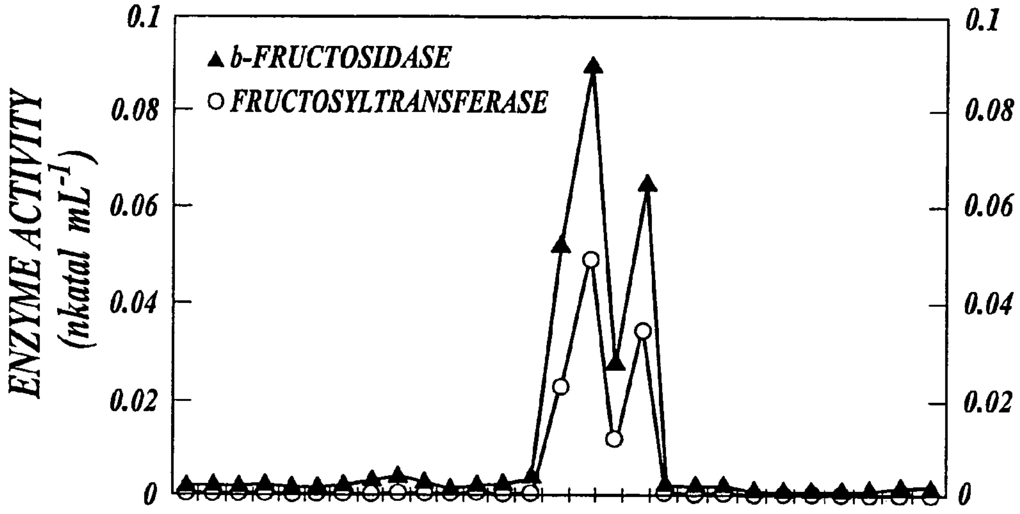
FIG. 7 is a graph of the enzymatic activity of a pool of fractions of 6-SFT after isoelectric focusing under non-denaturing conditions.
Figure 8:
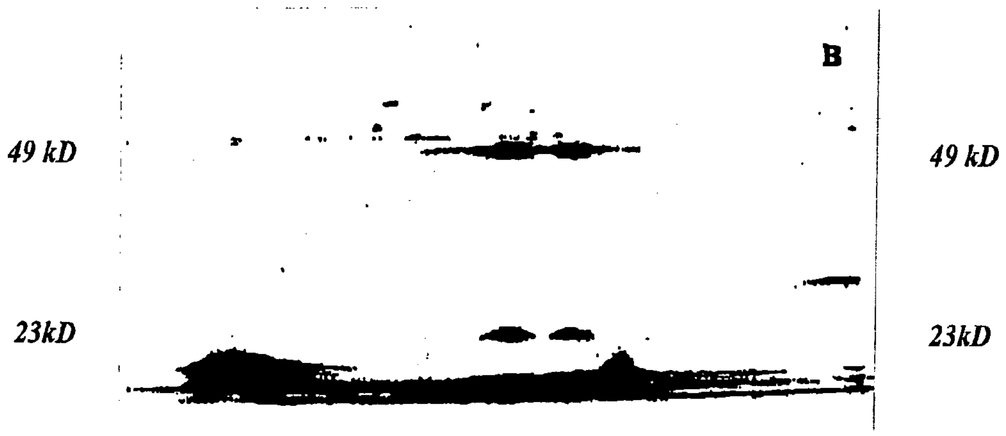
FIG. 8 is a photograph illustrating the SDS-PAGE gel after two-dimensional analysis of pool II of FIG. 6.
Figure 9:
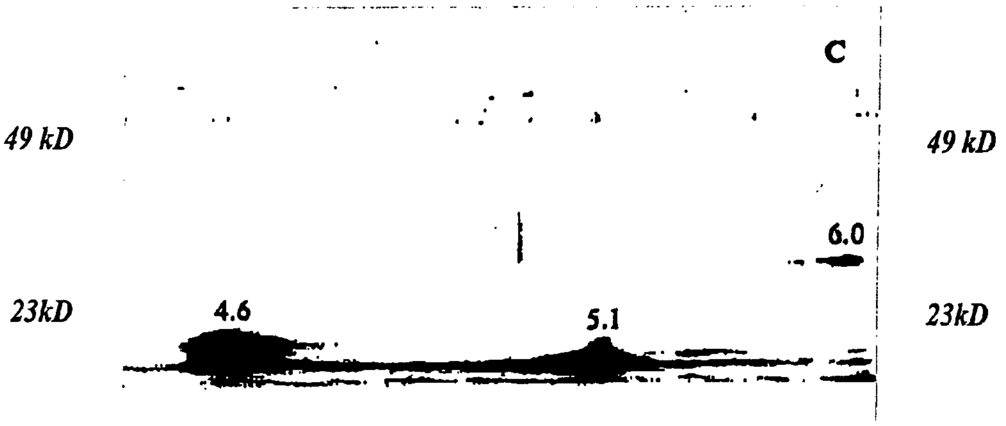
FIG. 9 is a photograph illustrating the two-dimensional gel electrophoreses of the IEF-markers phycocyanin, beta-lactoglobulin, and bovine carbonic anhydrase.

FIG. 7 shows a graph of the enzymatic activity of a pool of fractions of 6-SFT (referred to as pool II; see FIGS. 5 and 6A through 6D) after isoelectric focusing under non-denaturing conditions. Closed triangles indicate beta-fructosidase activity measured as released fructose, while open circles indicate the fructosyltransferase activity measured as formed kestose. FIG. 8 is an SDS-PAGE gel after two-dimensional analysis of pool II after the second anion exchange chromatography. The two 6-SFT isoforms are shown herein. Both isoforms are found to consist of two subunits of respectively 23 kDa and 49 kDa. FIG. 9 is the two-dimensional gel electrophoresis of the IEF-markers phycocyanin (pI 4.6), beta-lactoglobulin (pI 5.1) and bovine carbonic anhydrase (pI 6.0).

Figure 10:
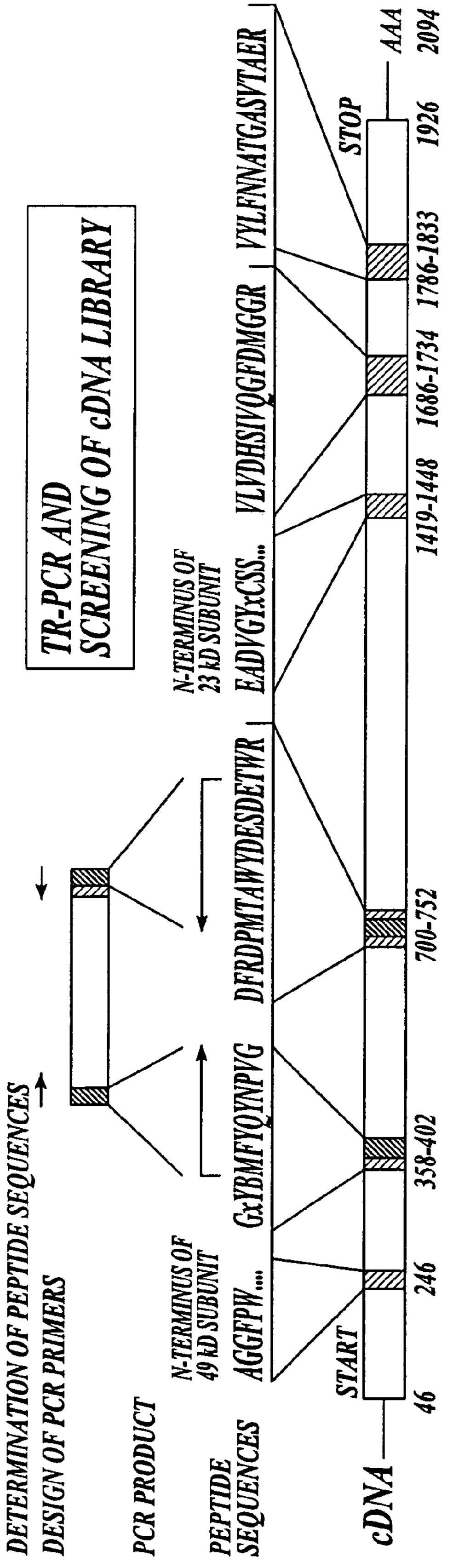
FIG. 10 is a schematic view of the strategy used to obtain the cDNA clone which codes for 6-SFT from barley.

FIG. 10 is a schematic view of the strategy used to obtain the cDNA clone which codes for 6-SFT from barley.

FIG. 8 shows the cDNA-sequence and the amino acid sequence of 6-SFT from barley derived therefrom.

Figure 11A:
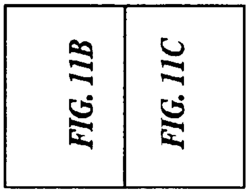
FIG. 11A illustrates the relationship between FIGS. 11B and 11C.

FIG. 11 is an overview of the derived amino acid sequence of 6-SFT from barley, different invertases (beta-fructosidases), levanases and levansucrases. The overview was produced with the Pileup program of the GCG sequence analysis software package. The following abbreviations were used:

H.v. 6-SFT=sucrose-fructan 6-fructosyltransferase from barley;

V.r. Inv=soluble acid invertase from green soya bean (mungbean; Arai et al., Plant Cell Physiol. 33, 245-252 (1992));

D.c. Inv=soluble acid invertase of carrot (Unger et al., Plant Physiol. 104, 1351-1357 (1994));

L.e. Inv=soluble acid invertase of tomato (Elliott et al., Plant Mol. Biol. 21, 515-524 (1993));

D.c. cw Inv=cell wall invertase of carrot (Sturm and Crispeels, Plant Cell 2, 1107-1119 (1990));

A.s. Inv=partial invertase sequence of oats (Wu et al., J. Plant Physiol. 142, 179-183 (1993));

E.c. Inv=invertase (rafD) of *Escherichia coli* (Aslandis et al., J. Bacteriol. 171, 6753-6763 (1989));

S.m. Scrb=invertase of *Streptococcus mutans* (Sato and Kuramitsu, Infect. Immun. 56, 1956-1960 (1989));

B.p. LelA=levanase from *Bacillus polymyxa* (Bezzate et al., non-published reference EMBO data base);

B.s. SacC=levanase of *Bacillus subtilis* (Martin et al., Mol. Gen. Genet. 208, 177-184 (1987));

K.m. Inu=inulinase of *Kluiveromyces marxianus* (Laloux et al., FEBS Lett. 289, 64-68 (1991));

S.c Inv1=invertase 1 of baking yeast (Hohmann and Gozalbo, Mol. Gen. Genet. 211, 446-454 (1988));

S.o. inv=invertase of *Schwanniomyces occidentalis* (Klein et al., Curr. Genet. 16, 145-152 (1989));

A.n.Inv=invertase of *Aspergillus niger* (Boddy et al., Curr. Genet. 24, 60-66 (1993));

B.a. SacB=levansucrase of *Bacillus amyloguefaciens* (Tang et al., Gene 96, 89-93 (1990));

B.s. SacB=levansucrase of *Bacillus subtilis* (steinmetz et al., Mol. Gen. Genet. 200, 220-228 (1985));

S.m. SacB=levansucrase of *Streptococcus mutans* (Shiroza and Kuramitsu, J. Bacteriol. 170, 810-816 (1988));

Z.m. LevU=levansucrase of *Zymomonas mobilis* (Song et al., non-published reference in EMBO data-base).

Figure 12:
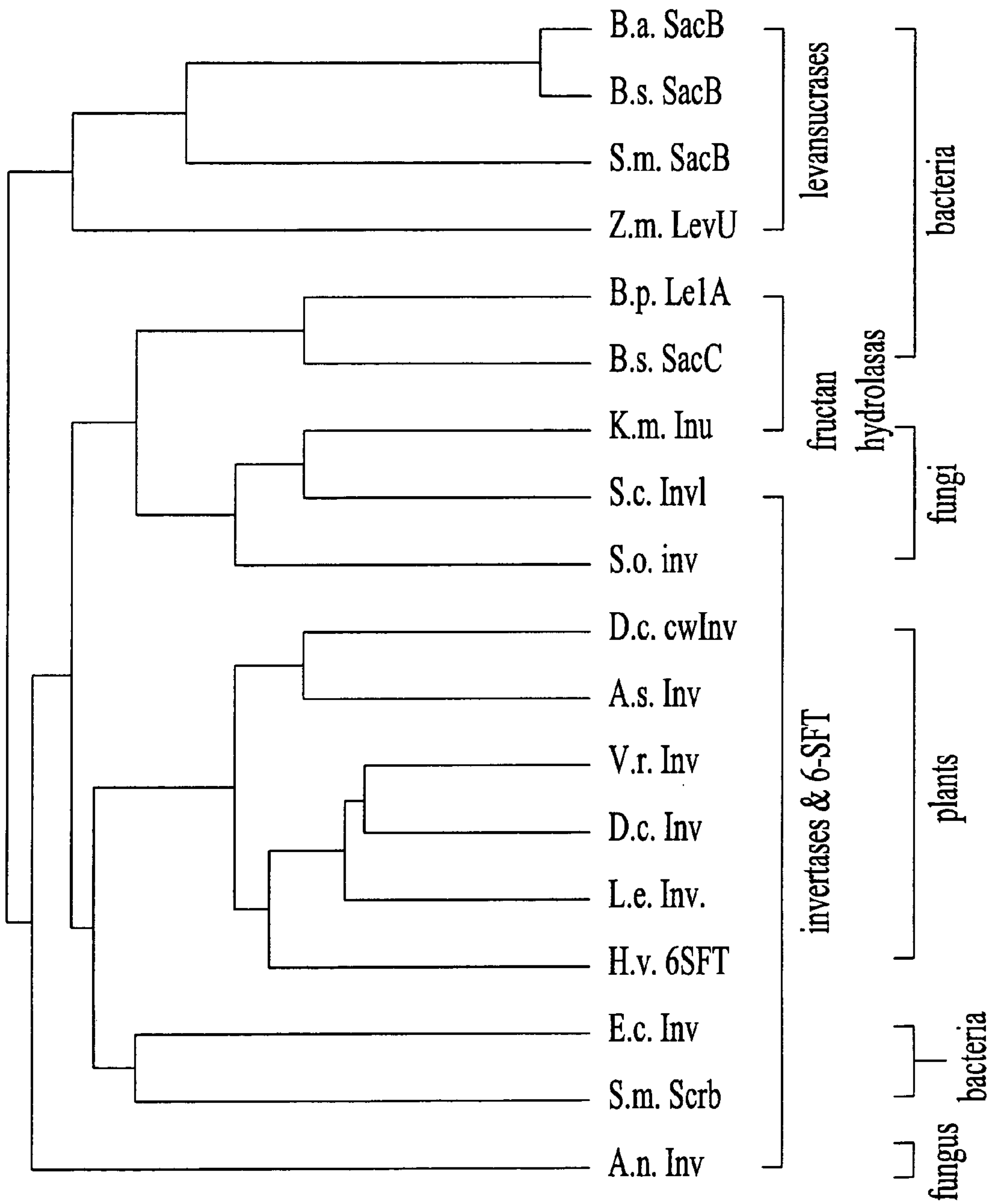
FIG. 12 is a dandrogram of 6-SFT from barley with different invertases, levanases and levansucrases, based on derived immunoacid sequences.

FIG. 12 is a dendrogram of 6-SFT from barley with different invertases (beta-fructosidases), levanases and levansucrases, based on derived amino acid sequences. The dendrogram was generated with the sequences described in FIG. 11 making use of the Pileup program of the GCG sequence analysis software package.

Figure 13:
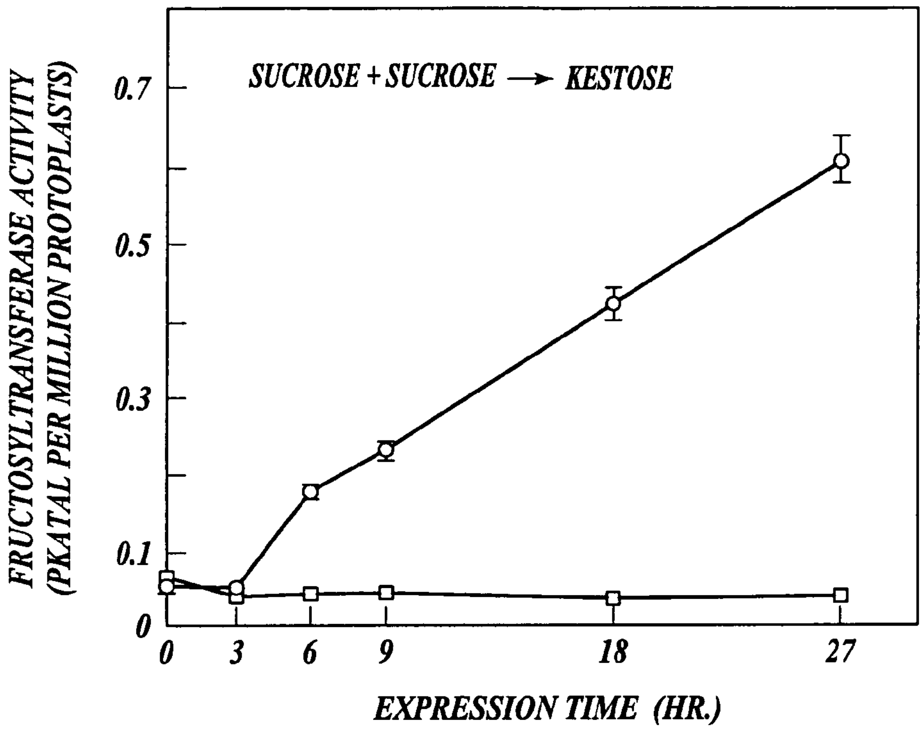
FIG. 13 is a graph illustrating the functional expression of barley 6-SFT in *Nicotiana plumbaginifolia* protoplasts.
Figure 14:
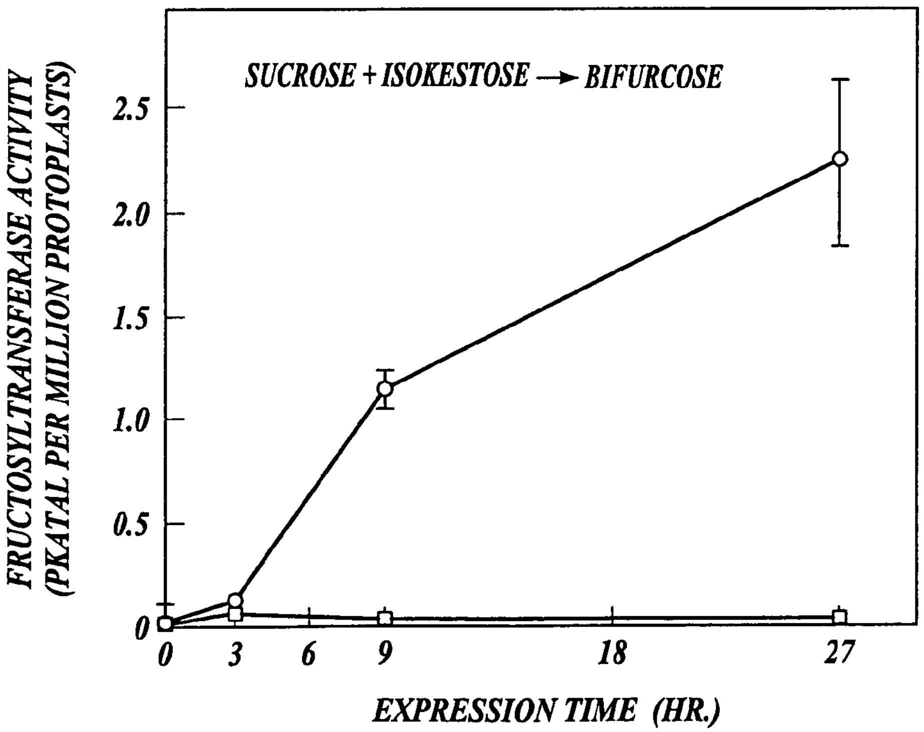
FIG. 14 is a graph illustrating the functional expression of barley 6-SFT in *Nicotiana plumbaginifolia* protoplasts.

FIGS. 13 and 14 show the functional expression of barley 6-SFT in *Nicotiana plumbaginifolia* protoplasts. Error bars indicate the average standard deviation. The 6-SFT cDNA was expressed for 27 hours in protoplasts. Samples were taken a number of times and the fructosyltransferase activity was determined in protoplast extracts by incubation with sucrose (FIG. 13) or sucrose and isokestose (FIG. 14). Open circles show the enzyme activity of extracts of protoplasts which were transformed with the 6-SFT gene construct. Open squares show the activity of extracts of protoplasts transformed with the vector without the 6-SFT cDNA.

Figure 15:
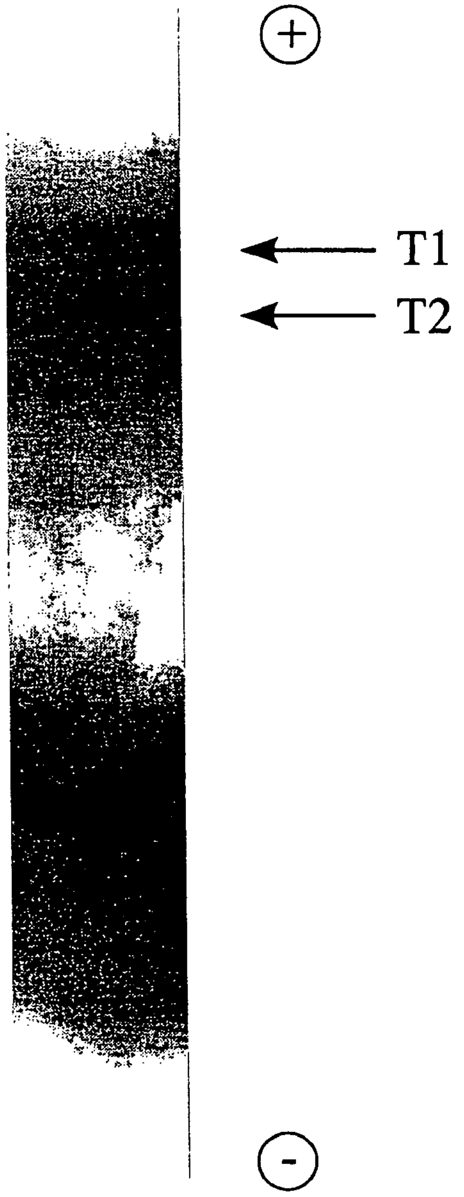
FIG. 15 is a photograph illustrating a native IEF-GEL of a purified enzyme extract of FFT from *Helianthus tuberosus* L.

FIG. 15 is a native IEF-gel of a purified enzyme extract of fructan-fructan fructosyltransferase (FFT) from *Helianthus tuberosus* L. After Coomassie Blue staining there can be seen in addition to the two most important isoforms of the FFT (T1 (pI 4.45) and T2 (pI 4.75)), a band with a pI of approximately 5.5, which probably corresponds with denatured FFT.

Figure 16:
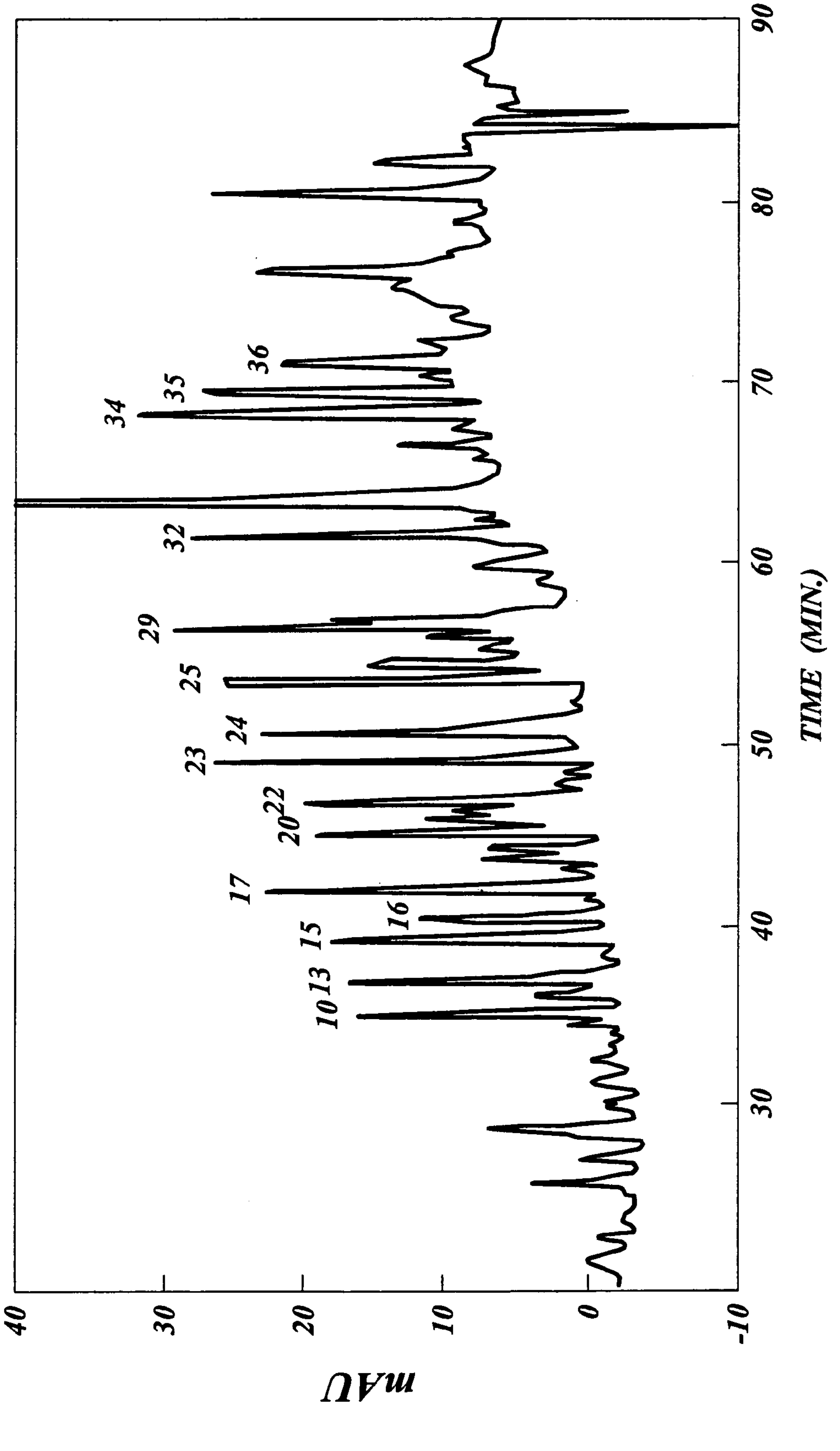
FIG. 16 is an HPLC-diagram of tryptic digests of the FFT isoform T1.
Figure 17:
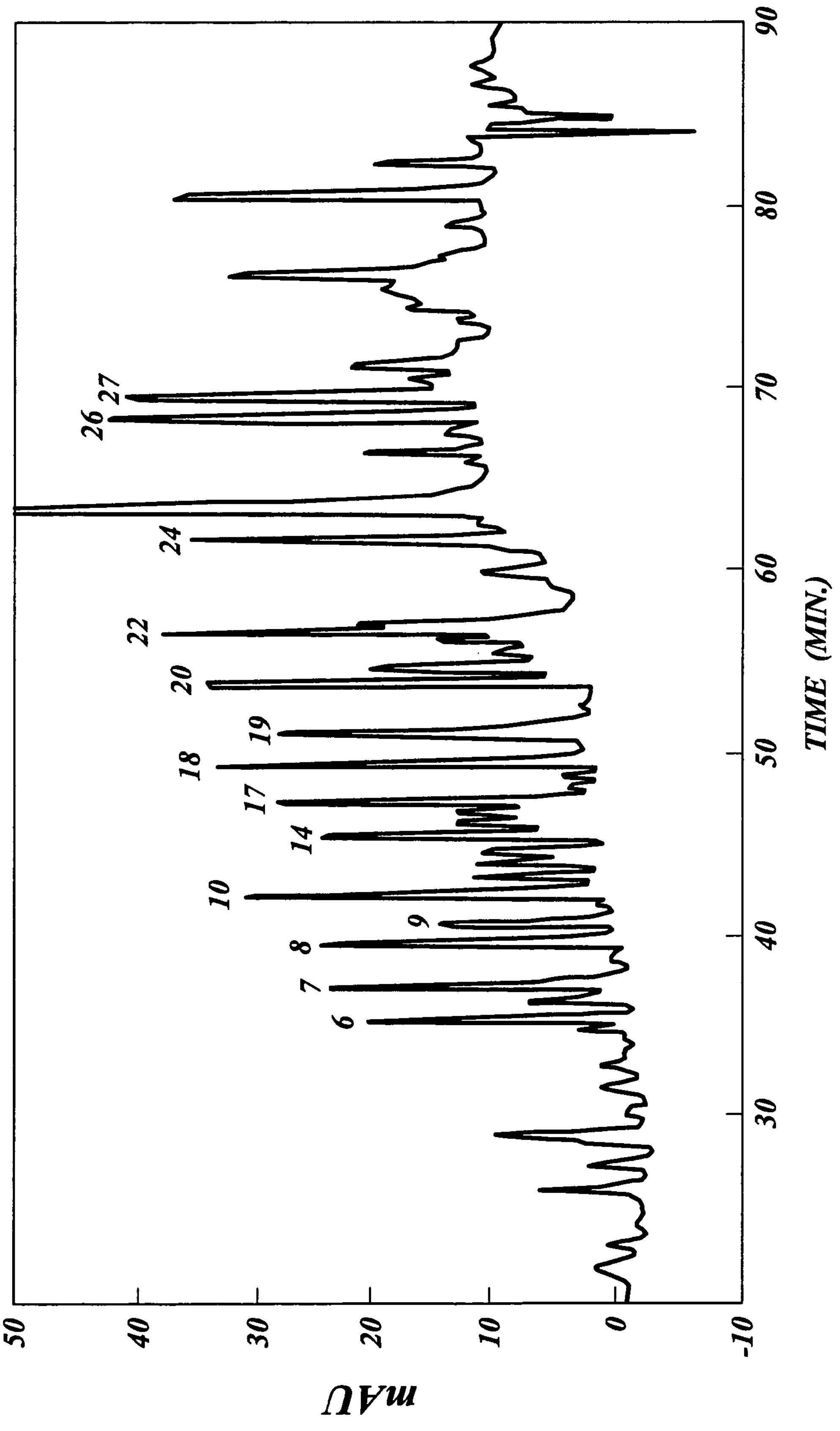
FIG. 17 is an HPLC-diagram of tryptic digests of the FFT isoform T2.

FIGS. 16 and 17 are HPLC-diagrams of tryptic digests of the FFT isoforms T1 (FIG. 16) and T2 (FIG. 17).

EXAMPLE 1

Selection of a Gene.

1. Naturally Occurring Genes

A large number of microbes were screened for their capacity to produce oligosaccharides from sucrose. For this purpose bacteria cultures were grown overnight in a liquid nutrient. The oligosaccharide-producing activity was determined by incubating a sample of the culture with 200 mM sucrose in the presence of 0.1% Triton X-100. The reaction products were separated by means of TLC and made visible using a fructose-specific reagent (Cairns, A. J. and Pollock, C. J., New Phytol. 109, 399-405 (1988)). It was found as a result of this screening that *Streptococcus mutant* is an effective producer of oligosaccharides (see FIG. 1). The oligosaccharide-producing enzymatic activity was purified from the *Streptococcus mutans* culture by means of DEAEion exchange chromatography and gel permeation chromatography. It was found herefrom that the enzymatic activity was caused by the product of the ftf gene previously described by shiroza and Kuramitsu, (J. Bacteriol. 170, 810-816 (1988)).

The fructosyltransferase (ftf) gene from plasmid pTS102 (Shiroza and Kuramitsu supra) was subsequently cloned as an EcoRV-BglII fragment in the multiple cloning site of pEMBL9 (Dente et al., Nucl. Acids Res. 11, 1645-1655 (1983)) and expressed from the lacZ promotor present in this plasmid. *E. coli* was then transformed herewith. The bacteria was hereby made capable of producing oligosaccharides.

The production of oligosaccharides was demonstrated by means of the screening method already mentioned above. Non-transformed *E. coli* does not produce any oligosaccharides from sucrose.

2. Mutated Genes

By means of mutagenesis it is possible to adapt the oligosaccharide-producing activity of the enzyme as required. Mutations in the gene can be brought about for instance in the following manner.

For mutagenesis of the ftf gene of *Streptococcus mutans*, the plasmid pTS102 was integrated into the genome of *Synechococcus sp*. PCC 7942 (R2-PIM9) by means of the genomic integration system (Van der Plas et al., Gene 95, 39-48 (1990)), which resulted in strain R2-PTS. This cyanobacteria R2-PTS strain expresses the fructosyltransferase gene. The R2-PTS strain is sucrose-sensitive due to polymer accumulation in the periplasm. An R2-PTS culture was mutated with N-methyl-N'-nitro-N-nitrosoguanidine (MNNG) which induces point mutations (T→C and G→A mutations). Mutants with a changed fructosyltransferase activity were selected. The culture mutated by means of MNNG was plated on sucrose-containing medium and a total of 400 sucrose-resistant colonies were tested for changed fructosyltransferase activity.

Derived from these colonies were R2-PTS cultures which were concentrated by means of centrifugation. The thus obtained pellets were resuspended in 50 mM sodium phosphate buffer with 1% Triton X-100, 200 mM sucrose and incubated overnight at 37° C. The reaction products were analysed by means of TLC-analysis (Cairns and Pollock, supra). The TLC was developed three times in 85:15 acetone:water and subsequently treated with atomized urea as described by Wise et al., Analytical Chemistry 27, 33-36 (1955). This method preferably stains fructose and fructose-containing polymers.

Of the mutants substantially producing trisaccharides, one was chosen for in vitro demonstration of the enzymatic oligosaccharide-forming activity of the mutated ftf gene in the above described manner.

According to the invention, other mutagenesis methods (site-directed or random) and genes which code for fructosyltransferases from other organisms can likewise be used to select a gene for a mutant oligosaccharide-producing protein.

EXAMPLE 2

Expression of the ftf Gene in Plants.

A. Construction of 35S-ftf-NOS in a Plant Transformation Vector.

The plasmid pMOG18 which contains a plant-specific 35S promotor with an enhancer duplication and sequences which stimulate the translations of mRNA is described by Symons et al., (Bio/Technology 8, 217-221 (1990). It contains the 35S-promotor-uidA-gene-NOS-terminator construct. A pBluescript II SK-plasmid from Stratagene (San Diego, Calif., U.S.A.), from which the internal BamHI-site was removed by digestion with BamHI and filling in the sticky ends with Klenow and ligating once again, was used for further cloning. The 35S-uidA-NOS-fragment was obtained by digestion with EcoRI and HindIII of pMOG18 and in this BamHI-pBluescript was cloned in the corresponding EcoRI/HindIII site, resulting in plasmid pPA2. Plasmid pPA2 was digested with NcoI and BamHI and the vector-containing fragment was isolated.

The fructosyltransferase gene ftf was cloned from the plasmid pTS102 (see above) as an EcoRV/BglII fragment in the multiple cloning site of pEMBL9. The compatible SmaI- and BamHI locations were used for this purpose. This resulted in the plasmid pTA12.

In order to obtain an NcoI location close to the mature processing site of the ftf gene (nucleotide position 783) (J. Bacteriol. 170, 810-816 (1988)), site-directed mutagenesis was performed as described by Kramer et al. (Nucleic Acids Res. 12, 9441-9456 (1984)) with the following oligonucleotide: 5'-GGCTCTCTTCTGTTCCATGGCAGATCAAGC-3'. (SEQ ID NO:3). Resulting therefrom was plasmid pTD2. At amino acid position +1 (nucleotide position 783) relative to the mature processing site a glutamine was hereby changed into a methionine. The NcoI/PstI fragment, in which the sequence coding for the mature fructosyltransferase is present, was used for further cloning. From this plasmid, the ftf gene was isolated as an NcoI/PstI fragment and this fragment was ligated in the pPA2 vector-containing fragment described above. This results in plasmid pTX. pTX contains the 35S-ftf-NOS-fragment in which ftf shows the mature fructosyltransferase gene without its signal sequence region. pTX was digested with XbaI and HindIII, the fragment containing the complete construct (35S-ftf-NOS) was cloned in the XbaI/HindIII restriction site of pMOG23 (Symons et al., supra) a derivative of the binary plant vector pBIN19 (Bevan, Nucl. Acids. Res. 12, 8711-8721). This resulted in plasmid pTZ.

B. Manufacture and Analysis of Transgenic Plants which Express the Mature ftf Gene.

The pTZ-plasmid was conjugated in *Agrobacterium tumefaciens* LB4404 (Hoekema et al., Nature 303, 179-180 (1983)) in a three-point crossbreeding making use of the helper plasmid pRK2013 (Lam, Plasmid 13, 200-204 (1985)). The construct was introduced into *Nicotiana tabacum* var. Petit Havanna (SR1) using the leaf disc transformation method (Horsch et al., Science 227, 1229-1232 (1985)). The regenerated plants were called KP-plants and were selected for kanamycine resistance and cultured on MS medium (Murashige and Skoog, Physiol. Plant. 15, 473-497 (1962)). Thereafter, the plants were grown on soil in the greenhouse and analysed.

The leaf material was cut off and ground in an eppendorf tube. After centrifugation (2 minutes at 16,000 rpm), 1 μl supernatant was analysed on TLC as described in Example 1.

Oligosaccharides were never found in wildtype plants or in plants which were transformed with non-related constructs. The screening of the transformants demonstrated oligosaccharide-accumulating plants using this method (see FIG. 2). The expression levels varied between individual plants which were transformed with the same construct. This is a normal phenomenon in transformation experiments in plants. The variation of the expression levels depends substantially on the integration position in the genome (position effect).

EXAMPLE 3

Oligosaccharide-producing Enzyme (SST) from the Onion.

In addition to the above used fructosyltransferase genes originating from micro-organisms, such enzymes are also produced by plants. In this example the SST gene from onion seed is used.

The SST protein from onion seed was purified by chromatographic procedures making use of the following protocol: the seed was incubated at 22° C. between moist cloths for 2 to 3 days and homogenised in 50 mM phosphate-citrate buffer with a pH of 5.7. The starch and debris were centrifuged off at about 10,000 g for 10 minutes. Ammonium sulphate was added to the supernatant to 20%, and the precipitate collected by centrifugation. The concentration of ammonium sulphate in the supernatant was increased to 80%, and the precipitate collected and dissolved in 20 mM NaAc pH 4.6. The solution was dialysed overnight with three buffer changes (20 mM NaAc) and the solution was clarified by centrifugation. The supernatant was placed on an FPLC monoS-column and eluted in 20 mM NaAc pH 4.6 with a 0-0.5 M NaCl gradient. After dialysis overnight against 10 mM NaAc pH 5.6, the solution was placed onto a raffinose-epoxy sepharose column (Pharmacia), which was equilibrated in 10 mM NaAc pH 5.6. Elution took place with a linear gradient consisting of 10 mM NaAc pH 5.6 (buffer A) and 10 mM phosphate-citrate buffer, pH 7.0, plus 0.5 M NaCl-buffer (buffer B). The active fractions were dialysed overnight against 20 mM phosphate-citrate buffer, pH 7.0, and placed on a monoQ FPLC-column in 20 mM phosphate-citrate buffer, pH 7.0. The column was eluted with a gradient of 0-0.5 M NaCl. For a final purification the protein was placed onto a Sepharose 6-column and eluted with 50 mM phosphate buffer, pH 6.5, 1% Triton-X-100. The silver staining of an SDS-PAGE gel of purified SST from onion seed revealed only one band with a molecular weight of approximately 68,000 d (see FIG. 3).

When this purified SST was incubated with sucrose, only 1-kestose was produced. No significant invertase activity was observed (see FIG. 4).

The amino acid sequence of the purified protein was determined on the basis of peptides obtained by gradual breakdown. On the basis of this information PCR-probes were designed with which the gene coding for the SST of onion seed was isolated. In the same manner as described in Examples 1 and 2, it was demonstrated both in vitro and in vivo that the gene codes for an enzyme capable of producing oligosaccharides.

EXAMPLE 4

Applicability with other Plant Species.

In order to illustrate the general applicability of the technology, the ftf construct described in Example 2 was introduced into different crops. The potato was thus transformed according to the method described in Visser, Plant Tissue Culture Manual B5, 1-9, Kluwer Academic Publishers, 1991. The resulting transgenic plants accumulated oligosaccharides in each tested organ. The same construct was also introduced into the beet (*Beta vulgaris* L.), which was transformed as described by D'Halluin et al., Biotechnology 10, 309-314 (1992). The resulting transgenic beet plants accumulated significant quantities of oligosaccharides in, for instance, their leaves and roots. The same constructs were introduced into *Brassica napus* L. which was transformed as according to Block et al., Plant Physiol. 91, 694-701 (1989). The resulting transgenic plants accumulated significant levels of oligosaccharides in, for instance, their leaves and storage organs. It is of course not essential that the plants are transformed in the manner indicated. Other methods within the reach of the skilled person can also be used.

Examples of other plant species which can be modified comprise, but are not limited to, maize (*Zea mays* L.), wheat (*Triticum aestivum* L.), barley (*Hordeum vulgare* L.), rice (*Oryza sativa* L.), soya bean (*Glycin max* L.), pea (*Pisum sativum* L.), bean (*Phaseolus vulgaris* L.), chicory (*Cichorium intybus* L.), sugar cane (*Saccharum officinarum* L.), sweet potato (*Dioscorea esculenta* L.), cassava (*Manihot esculenta* L.) and grasses (for instance *Lolium* spp., *Poa* spp. and *Festuca* spp.).

Plants with natural or induced modified carbohydrate separation patterns can be preferred target plants for the introduction of oligosaccharide-synthesizing genes. Such plants comprise, but are not limited to, natural mutants in starch and sucrose metabolism, and plants in which the starch and sucrose metabolism are modified by means of molecular and genetic techniques, as for instance described in Sonnewald and Willmitzer, Plant Physiology 99, 1267-1270, (1992).

EXAMPLE 5

Sucrose-fructan 6-fructosyltransferase (6-SFT) from Barley.

1. Introduction

Sucrose-fructan 6-fructosyltransferase (6-SFT) is a key enzyme for the biosynthesis of branched fructans (also called graminans) which are typical for grasses. The enzyme forms kestose from sucrose and bifurcose from sucrose and isokestose. In this example the purification of a 6-SFT from barley (*Hordeum vulgare* L.) is described, in addition to the cloning of the full cDNA and confirmation of the functionality.

2. Purification of sucrose-fructan 6-fructosyltransferase

Primary leaves of eight- to ten-day-old barley plants (*Hordeum vulgare* L. cv Express) were cut off and exposed to light continuously for 48 hours to induce the accumulation of fructans and enzymes of the fructan biosynthesis, as described by Simmen et al., Plant Physiol. 101, 459-468 (1993). The leaves were subsequently frozen in liquid nitrogen and stored at −70° C. until they were used.

An enzyme preparation was prepared by grinding induced primary leaves (700 g fresh weight) to a fine powder in liquid nitrogen and subsequently suspending them in extraction buffer (25 mM methylpiperazine, adjusted to pH 5.75 with HCl, with 1 mM DTT, 1 mM benzamidine, 1 mM EDTA, 0.1 mM PMSF and 0.5% PVP). 2 ml per g fresh weight hereof was used. After defrosting, the extract was kept at 4° C. and adjusted to pH 4.75 by adding 0.1 M HCl in drops while stirring. Three hours later the extract was centrifuged for 30 minutes at 17,000 g. The resulting supernatant was dialysed overnight at 4° C. against dialysis buffer (10 mM methylpiperazine (HCl) buffer (pH 5.75), with 1 mM DTT, 1 mM benzamidine, 1 mM EDTA and 0.1 mM PMSF).

The enzyme solution was purified by means of affinity chromatography on Blue Sepharose. For this purpose the enzyme solution was filtered through a 0.45 micrometer Millipore filter and loaded at a flow speed of 2 ml per minute on a column (26×120 mm) of Blue Sepharose-6-fast flow (Pharmacia, Uppsala, Sweden), which had previously been equilibrated with the above described dialysis buffer. In order to remove proteins without affinity for the dye, the column was washed with three bed volumes of the dialysis buffer. Bound proteins were eluted at a flow speed of 3 ml per minute (5 ml fractions), first with 0.2 M NaCl in 10 mM methylpiperazine (HCl) buffer (pH 5.75) for 30 minutes, followed by a linear gradient of 0.2 M to 0.5 M NaCl in the same buffer within 90 minutes.

All fractions which contained 6-SFT activity were pooled, dialysed overnight at 4° C. against dialysis buffer and then concentrated to one third of the starting volume by covering the dialysis bag with polyethylene glycol 40,000 and incubating it for 4 hours at 4° C.

For a first anion exchange chromatography step the 6-SFT fraction was filtered and loaded at a flow speed of 3 ml per minute on a 6 ml Resource Q column (Pharmacia), which had been equilibrated earlier with dialysis buffer. After the column was washed with 10 mM methylpiperazine (HCl) buffer (pH 5.75), the bound protein was eluted with a linear gradient of 0 to 0.15 M NaCl in the same buffer within 8 minutes at a flow speed of 15 ml per minute. Fractions of 1 ml were collected. The fractions which contained 6-SFT were pooled and supplemented with ammonium sulphate to a final concentration of 2 M.

The 6-SFT pool was subsequently subjected to hydrophobic interaction chromatography. For this purpose the pool was loaded at a flow speed of 0.5 ml per minute onto an alkylsuperose-column HR5/5 (Pharmacia) which had been equilibrated earlier with 50 mM citric acid-$Na_2HPO_4$ buffer (pH 5.0) with 2 M ammonium sulphate. The bound proteins were eluted within 60 minutes at a flow speed of 0.5 ml per minute with a linear gradient of 2 to 0 M ammonium sulphate in 50 mM citric acid-$Na_2HPO_4$ buffer (pH 5.0). Fractions of 0.5 ml were collected and the fractions which contained 6-SFT activity were pooled.

The pooled fractions were subjected to gel filtration chromatography and prior thereto first concentrated to a total volume of 190 microliters in microconcentrator centrifuge tubes (Centricon-30, Amicon-Grace, Beverly, Conn.). The concentrate was placed on a Superdex 75 HR 10/30 gel filtration column (Pharmacia), which was equilibrated with 100 mM citric acid-$Na_2HPO_4$ buffer (pH 5.75) with 0.2 M NaCl, and eluted with the same buffer at a flow speed of 0.4 ml per minute. Fractions of 0.2 ml were collected and the fractions containing 6-SFT activity were pooled and desalted by 5 successive concentrations and dilution steps in Centricon-30 microconcentrator centrifuge tubes with 10 mM methylpiperazine (HCl) buffer (pH 5.75).

For a second anion exchange chromatography step the desalted sample was loaded onto a 6 ml Resource Q column (Pharmacia). The conditions and buffers were the same as for the first anion exchange chromatography step but the fraction size was reduced to 0.5 ml. The fractions which contained 6-SFT activity were combined in pool I, II and III (FIG. 5).

During purification the enzymatic activity of the fractions was determined after the different purifying steps. For this purpose portions of 50-100 μl of the enzyme preparations were desalted by guiding them over Biogel P-10 columns (8×300 mm) by centrifugation at 350 g for 5 minutes (Simmen et al., supra). Desalted enzyme preparations were incubated with 0.2 M sucrose in 50 mM citric acid-$Na_2HPO_4$ buffer (pH 5.75) to identify fractions containing 6-SFT activity during the purification. The final enzyme preparations (pool I and III) were incubated with 0.1 M sucrose alone or in combination with 0.1 M isokestose in 25 mM methylpiperazine (HCl) buffer (pH 5.75). Unless otherwise indicated, the enzyme activity assays were performed for three hours at 27° C. The reaction was stopped by heating the samples for 3 minutes at 95° C. The samples were centrifuged for 5 minutes at 13,000 g, supplemented with trehalose (internal standard) to a final concentration of 0.1 μg/μl, and stored at −20° C. until the analysis.

Neutral carbohydrates were analysed by means of anion exchange chromatography on a CarboPac PA-100 column (Dionex, Sunnyvale, Calif., USA) with a Dionex DX-300 gradient chromatography system coupled to pulsed amperometric detection (Simmen et. al., supra). Prior to analysis by means of anion exchange chromatography, enzyme activities freeing glucose from sucrose were detected in the fractions collected during the enzyme purification using the glucose test kit (GOD-Perid method, Boehringer GmbH, Mannheim, Germany) in accordance with the instructions of the manufacturer.

Two 6-SFT isoforms with indistinguishable catalytic properties were isolated by the purification (see Table I). By affinity chromatography on the HighTrap blue column and by hydrophobic interaction chromatography on the alkylsuperose column, the invertase (beta-fructosidase) activity was almost completely separated from the 6-SFT. This means that 6-SFT has no invertase activity. The mol ratio between beta-fructosidase and fructosyltransferase activity fell by a factor of 6 after affinity chromatography and was then further reduced to a final ratio of approximately three after hydrophobic interaction chromatography (see Table I). The remaining beta-fructosidase activity could not be separated from 6-SFT and therefore appears to be one of its catalytic properties.

As already demonstrated by Simmen et. al., supra, its capacity to transfer fructose to either sucrose or to isokestose is a characterizing property of 6-SFT. Both 6-SFT isoforms which were obtained after the second anion exchange column have the same catalytic properties as shown by HPLC-analysis of the products formed after incubation with sucrose alone or with sucrose and isokestose (FIGS. 6A through 6D). In the presence of sucrose as the only substrate, mainly kestose is formed but sucrose is likewise hydrolysed to glucose and fructose. After incubation with sucrose and isokestose, mainly bifurcose is formed and much less sucrose is hydrolysed. This indicates that isokestose is the preferred acceptor compared with sucrose and that the beta-fructosidase activity is a component of the 6-SFT.

3. Gel Electrophoresis

To illustrate the purity of the two 6-SFT isoforms fractions of the Resource Q chromatography lying between the two 6-SFT peaks, and therefore containing both fractions, were pooled (pool II in FIGS. 5 and 6A through 6D) and analysed by non-denaturing IEF gel-analysis combined with either an enzyme activity assay (FIG. 7) or with SDS-PAGE analysis (FIG. 8).

For two-dimensional electrophoresis of 6-SFT pool II was subjected to isoelectric focussing within a pH range of 4-8 under non-denaturing conditions making use of a Mini-Protean II 2D-cell (Biorad) in accordance with the protocol of the manufacturer.

The 1 mm tubular gels were subsequently either cultured for 30 minutes in 5× sample buffer and loaded onto a 7.5-12% SDS polyacrylamide gel for a separation in the second dimension (Laemmli, Nature 227, 680-685 (1970)), or washed three times for ten minutes in 0.5 M citric acid $Na_2HPO_4$ buffer (pH 5.75) and cut into pieces of 2.5 mm for an enzyme activity assay. The 2.5 mm gel pieces were incubated in 0.4 M citric acid $Na_2HPO_4$ buffer (pH 5.75) with 0.2 M sucrose and 0.02% $NaN_3$ for 12 hours at 27° C. After centrifugation at 13,000 g for 5 minutes the supernatant was collected, heated to 95° C. for 3 minutes, supplemented with trehalose (internal standard, final concentration 0.1 μg/μl) and stored at −20° C. for further analysis.

Proteins separated on SDS-polyacrylamide gels were made visible by means of a silver staining (Blum, 1987).

The two isoforms were clearly separated and both had fructosyltransferase and likewise a beta-fructosidase activity. Their pI differed only slightly and was close to pH 5.0. After denaturation both 6-SFT isoforms provided on SDS-PAGE two subunits of respectively 49 and 23 kDa. This data and the almost complete identicity of the fragment patterns obtained by tryptic digestion (data not shown) indicate that the two isoforms display many similarities in structure and sequence. The negatively loaded 6-SFT (containing both isoforms) had a molecular weight of approximately 67 kDa as determined by size-exclusion chromatography (data not shown).

4. Determination of the N-terminal Amino Acid Sequence

For N-terminal amino acid sequence determination 100 μg protein of 6-SFT pool I and pool III was loaded onto a gradient gel (7.5-12%) and separated by SDS-PAGE (Laemmli, supra). The proteins were transferred to a polyvinylidene difluoride membrane (Immobilon PVDF transfer membrane, Millipore Corp., Bedford, Mass.) making use of the CAPS buffer system (Matsudeira, J. Biol. Chem 262, 10035-10038 (1987)). The protein bands were made visible on the membrane with 0.2% Ponceau S in 1% acetic acid, cut out and digested with trypsin.

Tryptic peptides were separated by reverse phase HPLC and N-terminal sequence determination of tryptic peptides was performed by automated Edman degradation.

The peptide sequence of the N-terminus of the 49 kDa subunit was determined and both, the large and the small, subunits were digested with trypsin in order to obtain internal peptide sequences. For both subunits two amino acid sequences of tryptic peptides were determined and used to design DNA primers (FIG. 10).

5. Design of a Probe

A 397 bp fragment was generated by reverse transcription polymerase chain reaction (RT-PCR). For this purpose single-strand cDNA was synthesized by reverse transcription of Poly($A^+$)-RNA making use of a synthetic oligo-d(T) primer (23 mer) and M-MUL V reverse transcriptase. PCR was performed according to the Perkin-Elmer protocol between the two synthetic, degenerated primers:

(i) CGCCTGCAGGTACCACATGTT(C/T)TA(C/T)CA(A/G)TA(C/T)AA(C/T)CC (SEQ ID NO:4); and (ii) CCACGTCTAGAGCTCTC(A/G)TC(A/G)TACCA(A/C/G)GC(C/G)GTCAT (SEQ ID NO:5).

These primers were designed in accordance with two part sequences of peptides obtained after tryptic digestion of 6-SFT. The resulting PCR product was cloned in the pCR-II™ vector (TA-cloning kit, Invitrogen). Labelling of the fragment with α-$^{32}$p-dATP was performed with a random primed labelling kit (Boehringer GmbH, Mannheim, Germany) according to the instructions of the manufacturer.

6. Screening of a cDNA Library

The fragment of 397 bp generated according to the method of paragraph 5 above was used as a probe in an RNA gel blot analysis of primary leaves, in which the accumulation of fructans was induced by continuous exposure to light for different tunes. There was found to be no hybridisation signal in the case of untreated leaves while a hybridising band of approximately 1800 bp accumulated rapidly in a manner which corresponded with the increase in 6-SFT activity in the leaves (data not shown). This result points to the presence of a messenger RNA of about 1800 bp in length.

The PCR product was also used to screen a cDNA expression library of primary leaves. A search was made here for a cDNA of full length.

To this end a cDNA expression library was first manufactured by extracting total RNA from 8 day-old cut primary leaves in which the synthesis of fructans was induced by continuous exposure to light for 48 hours. The leaves were ground in liquid nitrogen to a fine powder and suspended in RNA extraction buffer (0.1 M Trig (HCl), pH 9, with 10 mM EDTA, 0.1 M NaCl and 25 mM DTT). The still frozen sample was further ground until a cream-like consistency was reached and the sample was then extracted with phenol-chloroform-isoamylalcohol (25:24:1;v:v:v) (Brandt and Ingversen, Carlsberg Res. Commun. 43, 451-469 (1978)). The method was modified somewhat by omitting a second homogenisation step and by precipitating the RNA overnight with 2M LiCl at 4° C. after the last chloroform extraction. After a final ethanol precipitation poly (A)*-RNA was isolated by poly(U)-sepharose chromatography (Brandt and Ingversen, supra) and used for cDNA synthesis (ZAP-cDNA synthesis Kit, Stratagene, LaJolla, Calif., USA).

The cDNA was ligated in a uni-ZAP-XR vector, digested with EcoRI and XhoI and packaged in phage coats (Gigapack III Packaging Kit, Stratagene, La Jolla, Calif., USA) ($7.5\times10^7$ plaque-forming units per 5 μg poly(A)$^+$-RNA).

The primary library was screened with the α-$^{32}$P-labelled 397 bp long fragment of 6-SFT (see above) at 60° C. in accordance with the Stratagene protocol. Positive clones were screened once again and Bluescript phagmides were finally cleaved from the resulting positive phages using the Exassist/SOLR-system (strategene, La Jolla, Calif., USA). DNA sequencing of both strands was performed by the dideoxynucleotide sequencing method making use of the sequencing PRO kit (Toyobo, Osaka, Japan). Unless indicated otherwise, standard protocols were used (Sambrook et al., Cold Spring Harbor Laboratory Press, Cold Spring Harbor (1989)). Sequence data-analysis was carried out using the GCG sequence analyses software package, version 7.2 (1992).

After the first screening 9 positive clones were isolated. After a further screening, 7 clones remained positive. Of these the sequence was partially determined from the 5' terminus and from the internal primers which were designed on the basis of the PCR product. All 7 clones appeared to code for the same protein, and four of them comprised the complete coding sequence. Of one of the possible clones of full length the sequence was wholly determined on both strands and it was found that it coded for a polypeptide which contained the 49 kDa subunit as well as the 23 kDa subunit (FIG. 10).

The complete nucleotide sequence of the fully sequenced cDNA (SEQ ID NO:1) comprises one long open reading frame which begins at nucleotide 46 and ends at nucleotide 1923 for two stop codons. The open reading frame codes for a polypeptide chain of 626 amino acids including a leader sequence of 67 residues in length.

The mature 6-SFT starts at nucleotide 246 and therefore has at least 559 amino acid residues with a calculated molecular weight of 61.3 kDa and a calculated pI of 5.37. All 5 of the partial amino acid sequences obtained from the purified protein are present in the amino acid sequence (SEQ ID NO:2) derived from the cDNA. The cDNA likewise contains 45 bp of a 5' non-translated and 171 bp of a 3' non-translated sequence with a poly(A) tail. A possible translation initiation signal (ATG) of the 6-SFT cDNA is localized at the nucleotide positions 46 to 48 and a possible polyadenylating sequence is present at the nucleotide positions 1973 to 1979. It has been found that the mature 6-SFT displays alpha-methyl-mannoside-reversible binding on ConA-Sepharose, which indicates that it is a glycoprotein (data not shown). Similarly, the derived amino acid sequence contains 6 possible glycosylating positions (Asn-X-Ser/Thr).

All peptide sequences obtained from the purified protein are situated without any mismatch in the derived amino acid sequence. The two peptide sequences obtained from the 23 kDa subunit of the purified SFT are localized close to the 3'-terminus of the cDNA, while the sequences obtained from the 49 kDa subunit are localized in the vicinity of the 5'-terminus.

In order to study the possible relation of the cDNA to known beta-fructosidases and fructosyltransferases, the derived amino acid sequence was compared with the sequence of different vegetable, fungal and bacterial invertases, and with bacterial levanases and levansucrases (FIG. 15 and FIG. 16). The cDNA described herein has the highest homology with soluble acid invertases of the green soya bean (mungbean) (Arai et al., supra), carrot (Unger et al., supra), and tomato (Elliott et al., supra), and equally clear homologies with invertases, levanases and levansucrases from other kingdoms, that is, with a number of beta-fructosidases. The comparison of the amino acid sequence indicates at least five well conserved domains. Domains I (SEQ ID NO:6) and IV (SEQ ID NO:7) are less conserved between invertases and levansucrases than domains II (SEQ ID NO.:8), III (SEQ ID NO:9) and V (SEQ ID NO:10). With these enzymes domain III in particular is very conserved. Surprisingly, the most limited homology is that with bacterial levansucrases, that is, with a class of enzymes which catalyse a similar 6-fructosyl transfer reaction as 6-SFT (see the dendrogram in FIG. 16).

7. Expression of 6-SFT in *Nicotiana plumbaginifolia* Protoplasts

The 6-SFT cDNA clone was sub-cloned in a derivative of the pUC119 plasmid vector (Sambrook et al., Molecular Cloning, A Laboratory Manual, Cold Spring Harbor Laboratory Press, Cold Spring Harbor (1989)) under the regulation of the expression signals of the cauliflower mosaic virus 35S transcript (Neuhaus et al., Proc. Natl. Acad. Sci. USA 88, 10362-10366 (1991)).

Protoplasts of *Nicotiana plumbaginifolia* were isolated and transformed largely as described by Goodall et al. (Meth. Enzymol. 181, 148-161 (1990)). In summary, 10 μg of the plasmid containing the 6-SFT cDNA was dispersed in a Volume of 10 μl TE buffer in sterile 15 ml plastic tubes. Control transformations were carried out with 10 μg of the same plasmid without insert. $1\times10^6$ protoplasts were added up to a volume of 0.5 ml and mixed carefully with an equal volume 20% (w/v) polyethylene glycol 6000. After 2-5 minutes 6.5 ml K3 medium was added and the protoplasts incubated for two hours at 27° C. They were thereafter diluted 1:1 with the W5 osmoticum and pelleted for 10 minutes at 1000 g. All protoplasts (except those which were taken as control at t=0 hour) were resuspended in 2 ml K3 medium and incubated at 27° C. After 3, 6, 9, 18 and 27 hours samples were taken for product analysis. The protoplasts were herein pelleted for 10 minutes at 1000 g after addition of 2 ml W5 osmoticum. The protoplast pellet was resuspended in 0.1 M citric acid $Na_2HPO_4$ buffer (pH 5.75), transferred to sterile Eppendorf tubes and frozen in liquid nitrogen. After defrosting the samples were vortexed, and cell debris was pelleted at 13.000 g for 3 minutes. The supernatants (50 to 100 μl ) were desalted by guiding them over Biogel P-10 columns as described above. Desalted enzyme samples were incubated with 0.1 M sucrose or with 0.1 M sucrose in combination with 0.1 M isokestose in 50 mM citric acid $Na_2HPO_4$ buffer (pH 5.75) with 0.02% $NaN_3$ for 20 hours at 27° C. The product analysis was performed as described in the case of FIGS. 5 and 6A through 6D after stopping of the reaction by heating the samples at 95° C. for 3 minutes.

After an initial lag-phase of about 3 hours extracts of protoplasts formed kestose from sucrose and bifurcose from sucrose and isokestose. This confirms that the cDNA codes for a functional 6-SFT (FIG. 12). Like the purified enzyme, the activity present in the protoplasts catalysed the production of bifurcose from sucrose and isokestose at a speed that was roughly four times higher than the production of isokestose from sucrose. These results confirm that the cDNA codes for a 6-SFT.

EXAMPLE 6

Fructan-fructan Fructosyltransferase from Jerusalem Artichoke

Another vegetable fructosyltransferase for application in the invention was purified from Jerusalem artichoke (*Helianthus tuberosus* L.) by means of the Lüscher method (Lüscher M. et al., New Phytol. 123, 717-724 (1993)) using salt precipitation, lectin-affinity chromatography and ion exchange chromatography.

The purified enzyme was separated on a native IEF-gel and blotted on a PVDF membrane. The membrane was stained by means of a Coomassie Blue staining and the two most important FFT isoforms (respectively T1 and T2) were cut out (see FIG. 15).

Both proteins T1 and T2 were digested with trypsin and the peptides were separated by means of HPLC. The HPLC-diagrams of the digested FFT isoforms exhibit identical patterns (see FIGS. 16 and 17). The amino acid sequence was determined of two of the purified peptides of T2 (fractions 18 and 24). The sequence of the first peptide was:

$NH_2$-E-Q-W-E-G-X-F-M-Q-Q-Y-X-X-(SEQ ID NO:11).

The other peptide had the following amino acid sequence:

$NH_2$-A-V-P-V-X-L-X-X-P-L-(F/L)-I-X-W-V-(SEQ ID NO:12).

In the same manner as in Example 5 the cDNA was isolated and the sequence determined. Using a complete cDNA-clone plant cells were transformed to obtain transgenic plants.

EXAMPLE 7

Use of the Oligosaccharides According to the Invention

The oligosaccharides produced using the method according to the invention can be used as sugar substitutes in different products. Three examples hereof are given below.

1. Ice Cream

Ice cream is prepared from the following ingredients:

| | |
|---|---|
| 635 | parts water |
| 90 | parts butter fat |
| 100 | parts low-fat milk powder |
| 170 | parts oligosaccharides according to the invention |
| 5 | parts Cremodan SE30 ™ (Grindsted) |
| 0.3 | parts Aspartame ™ |
| | flavourings as required. |

The milk powder is dissolved in the water. The whole is heated to 40-45° C. The remaining dry ingredients are mixed and dissolved in the warm milk. The melted butter is then added. This whole is then pasteurised for 10 minutes at 72° C. The mixture is thereafter homogenised in a two-stage homogenizer at 150/35 bar. The ice mix obtained is cooled rapidly to 5° C. and the whole is subsequently left to mature for a minimum of 4 hours at 5° C. Finally, the ice mix is aerated and frozen to an overrun of 100%.

After hardening at −35° C. and storage at −20° C. an ice cream is obtained which corresponds in terms of taste and texture with ice cream prepared with natural sugars (saccharose, glucose syrup).

2. Muesli Bar

A muesli bar was prepared from the following ingredients:

| | |
|---|---|
| 28 | parts oligosaccharides according to the invention |
| 68 | parts muesli mix |
| 4 | parts cacao |

A syrup was produced from the oligosaccharides by heating, which syrup was mixed with the other ingredients. The bars were formed from the thus obtained mixture in a cylindrical press. Due to the omission of natural sugar the bar is much lower calorie than conventional bars.

3. Soft Drink

A soft drink was prepared from the following ingredients:

| | |
|---|---|
| 90 | parts water or fruit juice |
| 8-10 | parts oligosaccharides according to the invention |
| | artificial sweeteners |
| | flavourings and coloring agents |
| | nutrient acid |
| | carbon dioxide |

All ingredients were dissolved in a part of the water. The remaining water was then added as carbon dioxide-containing water. The energy value of the soft drink is much less because no additional natural sugars are added.

TABLE I

Purification of 6-SFT

| Purification step | fructosyltransferase nkatal[c] | fructosyltransferase % | Protein mg | Purification -fold | β-fructosidase/-fructosyltransferase[b] mol ratio |
|---|---|---|---|---|---|
| Crude extract | 243 | 100 | 5000 | 1 | 32 |
| Acid precipitation | 159 | 66 | 1700 | 2 | 29 |
| High-Trap-blue | 71.6 | 29 | 450 | 3 | 5.7 |
| First Resource Q | 22.6 | 9.3 | 79 | 6 | 6.2 |
| Alcyl Superose | 9.32 | 3.8 | 56 | 4 | 3.2 |
| Superdex 75 | 6.64 | 2.7 | 9.5 | 15 | 3.4 |
| Second Resource Q pool I | 2.99 | 1.2 | 0.6 | 103 | 2.7 |
| Second Resource Q pool II | 4.33 | 1.8 | 1.7 | 52 | 3.2 |

[a]measured as kestose-producing activity

[b]mol fructose per mol produced fructose

[c]nkatal = nmol · $s^{-1}$

The invention claimed is:

1. A method for producing oligosaccharides having a low degree of polymerization, comprising the steps of:

(a) selecting a vegetable gene which encodes a fructosyltransferase enzyme which converts sucrose into an oligosaccharide having a low degree of polymerization;

(b) linking the vegetable gene to suitable transcription-initiation and transcription-termination signals to provide an expression construct;

(c) transforming a plant cell from a mutant plant having an altered starch or sucrose metabolism with the expression construct;

(d) regenerating a transgenic plant from the transformed plant cell;

(e) culturing the transgenic plant under conditions enabling the expression and activity of the fructosyltransferase enzyme; and (f) isolating the oligosaccharides from the transgenic plant.

2. The method of claim 1, wherein the mutant plant having an altered starch or sucrose metabolism is naturally occurring.

3. The method of claim 1, wherein the mutant plant having an altered starch or sucrose metabolism has been modified by means of molecular and genetic techniques.

4. A method for producing food products comprising oligosaccharides having a low degree of polymerization as a sugar substitute, comprising the steps of:

(a) selecting a vegetable gene which encodes a fructosyltransferase enzyme which converts sucrose into an oligosaccharide having a low degree of polymerization;

(b) linking the vegetable gene to suitable transcription-initiation and transcription-termination signals to provide an expression product;

(c) transforming a plant cell from a mutant plant having an altered starch or sucrose metabolism with the expression construct;

(d) regenerating a transgenic plant from the transformed plant cell;

(e) culturing the transgenic plant under conditions enabling the expression and activity of the fructosyltransferase enzyme;

(f) isolating the oligosaccharides from the transgenic plant; and (g) incorporating the oligosaccharides as a sugar substitute into the food products.

* * * * *

UNITED STATES PATENT AND TRADEMARK OFFICE

CERTIFICATE OF CORRECTION

PATENT NO. : 7,314,973 B2
APPLICATION NO. : 10/691346
DATED : January 1, 2008
INVENTOR(S) : J. C. M. Smeekens et al.

It is certified that error appears in the above-identified patent and that said Letters Patent is hereby corrected as shown below:

| **COLUMN** | **LINE** | **ERROR** |
|---|---|---|
| Title Page (56) Pg. 1, col. 2 | Refs. Cited (Foreign Pats., Item 17) | Delete as duplicative "WO WO91/13076 9/1991" |
| Title Page (56) Pg. 1, col. 2 | Refs. Cited (Foreign Pats., Item 24) | Delete as duplicative "WO WO95/13389 * 5/1995" |
| Title Page Pg. 1, col. 2 | Assistant Examiner | "Brent T Page" should read --Brent T. Page-- |
| Col. 1 | Ln. 8 | "abandoned which" should read --abandoned, which-- |
| Col. 1 | Ln. 50 | "oligof-ructose" should read --oligo-fructose-- |
| Col. 3 | Ln. 32 | "iso forms" should read --isoforms-- |
| Col. 4 | Ln. 24 | "invention. It" should read --invention, it-- |
| Col. 4 | Ln. 35 | "(for example" should read --(for example,-- |
| Col. 4 | Ln. 38 | "*tobacter*)" should read --*tobacter*),-- |
| Col. 4 | Ln. 40 | "*Rothia*)" should read --*Rothia*),-- |
| Col. 4 | Ln. 41 | "*tenuis*)." should read --*tenius*).-- |

UNITED STATES PATENT AND TRADEMARK OFFICE
CERTIFICATE OF CORRECTION

PATENT NO. : 7,314,973 B2
APPLICATION NO. : 10/691346
DATED : January 1, 2008
INVENTOR(S) : J. C. M. Smeekens et al.

It is certified that error appears in the above-identified patent and that said Letters Patent is hereby corrected as shown below:

| COLUMN | LINE | ERROR |
|---|---|---|
| Col. 7 | Ln. 17 | "**6**D" should read --**6**D)-- |
| Col. 7 | Ln. 46-47 | delete "FIG. **8** shows the cDNA-sequence and the amino acid sequence of 6-SFT from barley derived therefrom." |
| Col. 8 | Ln. 17 | "(steinmetz" should read --(Steinmetz-- |
| Col. 8 | Ln. 22 | "data-base)." should read --database).-- |
| Col. 9 | Ln. 4 | "shiroza" should read --Shiroza-- |
| Col. 10 | Ln. 24 | ". . .CAAGC-" should read -- . . .GAAGC- -- |
| Col. 11 | Ln. 8 | "above used" should read --above-used-- |
| Col. 11 | Ln. 10 | "example" should read --example,-- |
| Col. 11 | Ln. 38 | "6.5, 1%" should read --6.5, with 1%-- |
| Col. 11 | Ln. 38 | "Triton-X-100." should read --Triton X-100®.-- |

UNITED STATES PATENT AND TRADEMARK OFFICE

CERTIFICATE OF CORRECTION

PATENT NO. : 7,314,973 B2
APPLICATION NO. : 10/691346
DATED : January 1, 2008
INVENTOR(S) : J. C. M. Smeekens et al.

It is certified that error appears in the above-identified patent and that said Letters Patent is hereby corrected as shown below:

| COLUMN | LINE | ERROR |
|---|---|---|
| Col. 13 | Ln. 13 | "buffer and" should read --buffer, and-- |
| Col. 16 | Ln. 17 | "Trig" should read --Tris-- |
| Col. 16 | Ln. 33 | "Poly(A+)-" should read --Poly($A^+$)-- |
| Col. 16 | Ln. 39 | "strategene," should read --Stratagene,-- |
| Col. 17 | Ln. 57 | "Volume" should read --volume-- |

Signed and Sealed this

Third Day of February, 2009

JOHN DOLL
*Acting Director of the United States Patent and Trademark Office*

SEQUENCE LISTING

<160> NUMBER OF SEQ ID NOS: 12

<210> SEQ ID NO 1
<211> LENGTH: 2094
<212> TYPE: DNA
<213> ORGANISM: Barley
<220> FEATURE:
<221> NAME/KEY: CDS
<222> LOCATION: (46)..(1923)

<400> SEQUENCE: 1
gctcagaatc taccaaaccc tctcggagtt gacgagcggc gccgc atg ggg tca cac 57
Met Gly Ser His
1 ggc aag cca ccg cta ccg tac gcc tac aag ccg ctg ccc tcg gac gcc 105
Gly Lys Pro Pro Leu Pro Tyr Ala Tyr Lys Pro Leu Pro Ser Asp Ala
5 10 15 20 gcc gac ggt aag cgg acc ggc tgc atg agg tgg tcc gcg tgt gcc acc 153
Ala Asp Gly Lys Arg Thr Gly Cys Met Arg Trp Ser Ala Cys Ala Thr
25 30 35 gtg ctg acg gcc tcg gcc atg gcg gtg gtg gtg gtc ggc gcc acg ctc 201
Val Leu Thr Ala Ser Ala Met Ala Val Val Val Val Gly Ala Thr Leu
40 45 50 ctg gcg gga ttg agg atg gag cag gcc gtc gac gag gag gcg gcg gcg 249
Leu Ala Gly Leu Arg Met Glu Gln Ala Val Asp Glu Glu Ala Ala Ala
55 60 65 ggc ggg ttc ccg tgg agc aac gag atg ctg cag tgg cag cgc agc ggt 297
Gly Gly Phe Pro Trp Ser Asn Glu Met Leu Gln Trp Gln Arg Ser Gly
70 75 80 tac cat ttc cag acg gcc aag aac tac atg agc gat ccc aac ggc ctg 345
Tyr His Phe Gln Thr Ala Lys Asn Tyr Met Ser Asp Pro Asn Gly Leu
85 90 95 100 atg tat tac cgt gga tgg tac cac atg ttc tac cag tac aac ccg gtg 393
Met Tyr Tyr Arg Gly Trp Tyr His Met Phe Tyr Gln Tyr Asn Pro Val
105 110 115 ggc acc gac tgg gac gac ggc atg gag tgg ggc cac gcc gtg tcc cgg 441
Gly Thr Asp Trp Asp Asp Gly Met Glu Trp Gly His Ala Val Ser Arg
120 125 130 aac ctt gtc caa tgg cgc acc ctc cct atc gcc atg gtg gcc gac cag 489
Asn Leu Val Gln Trp Arg Thr Leu Pro Ile Ala Met Val Ala Asp Gln
135 140 145 tgg tac gac atc ctc gga gtc ctc tcg ggc tcc atg acg gtg cta ccc 537
Trp Tyr Asp Ile Leu Gly Val Leu Ser Gly Ser Met Thr Val Leu Pro
150 155 160 aac ggg acg gtc atc atg atc tac acg ggc gcc acc aac gcc tcc gcc 585
Asn Gly Thr Val Ile Met Ile Tyr Thr Gly Ala Thr Asn Ala Ser Ala
165 170 175 180 gtg gag gtc cag tgc atc gcc acc ccg gcc gac ccc aac gac ccc ctc 633
Val Glu Val Gln Cys Ile Ala Thr Pro Ala Asp Pro Asn Asp Pro Leu
185 190 195 ctc cgc cgg tgg acc aag cac ccc gcc aac ccc gtc atc tgg tcg ccg 681
Leu Arg Arg Trp Thr Lys His Pro Ala Asn Pro Val Ile Trp Ser Pro
200 205 210 ccg ggg gtc ggc acc aag gat ttc cga gac ccg atg acc gcc tgg tac 729
Pro Gly Val Gly Thr Lys Asp Phe Arg Asp Pro Met Thr Ala Trp Tyr
215 220 225 gac gag tcc gac gag aca tgg cgc acc ctc ctc ggg tcc aag gac gac 777
Asp Glu Ser Asp Glu Thr Trp Arg Thr Leu Leu Gly Ser Lys Asp Asp
230 235 240

-continued cac gac ggc cac cac gac ggc atc gcc atg atg tac aag acc aag gac 825
His Asp Gly His His Asp Gly Ile Ala Met Met Tyr Lys Thr Lys Asp
245 250 255 260 ttc ctc aac tac gag ctc atc ccg ggc atc ttg cac cgg gtg gtg cgc 873
Phe Leu Asn Tyr Glu Leu Ile Pro Gly Ile Leu His Arg Val Val Arg
265 270 275 acc ggc gag tgg gag tgc atc gac ttc tac ccc gtc ggc cgg aga agc 921
Thr Gly Glu Trp Glu Cys Ile Asp Phe Tyr Pro Val Gly Arg Arg Ser
280 285 290 agc gac aac tcg tcg gag atg ctg cac gtg ttg aag gcg agc atg gac 969
Ser Asp Asn Ser Ser Glu Met Leu His Val Leu Lys Ala Ser Met Asp
295 300 305 gac gaa cgg cac gac tac tac tcg ctg ggc acg tac gac tcg gcg gcc 1017
Asp Glu Arg His Asp Tyr Tyr Ser Leu Gly Thr Tyr Asp Ser Ala Ala
310 315 320 aac acg tgg acg ccc atc gac ccg gag ctc gac ttg ggg atc ggg ctg 1065
Asn Thr Trp Thr Pro Ile Asp Pro Glu Leu Asp Leu Gly Ile Gly Leu
325 330 335 340 aga tac gac tgg gga aag ttt tat gcg tcc acc tcc ttc tat gat ccg 1113
Arg Tyr Asp Trp Gly Lys Phe Tyr Ala Ser Thr Ser Phe Tyr Asp Pro
345 350 355 gcc aag aac cgg cgc gtg ctc atg ggg tac gtc ggc gag gtc gac tcc 1161
Ala Lys Asn Arg Arg Val Leu Met Gly Tyr Val Gly Glu Val Asp Ser
360 365 370 aag cgg gct gat gtc gtc aag gga tgg gct tcc att cag tca gtt cct 1209
Lys Arg Ala Asp Val Val Lys Gly Trp Ala Ser Ile Gln Ser Val Pro
375 380 385 agg acg gtg gct ctg gat gag aag acc cgg acg aac ctc ctg ctc tgg 1257
Arg Thr Val Ala Leu Asp Glu Lys Thr Arg Thr Asn Leu Leu Leu Trp
390 395 400 ccc gtt gag gag atc gag acc ctc cgc ctc aat gcc acg gaa ctg acc 1305
Pro Val Glu Glu Ile Glu Thr Leu Arg Leu Asn Ala Thr Glu Leu Thr
405 410 415 420 gac gtt acc att aac act ggc tcc gtc atc cat atc ccg ctc cgc caa 1353
Asp Val Thr Ile Asn Thr Gly Ser Val Ile His Ile Pro Leu Arg Gln
425 430 435 ggc act cac gct cga cat gcg gag gcc tct ttc cac ctt gat gct tcc 1401
Gly Thr His Ala Arg His Ala Glu Ala Ser Phe His Leu Asp Ala Ser
440 445 450 gcc gtg gct gcc ctc aac gag gcc gat gtg ggc tac aac tgc agt agc 1449
Ala Val Ala Ala Leu Asn Glu Ala Asp Val Gly Tyr Asn Cys Ser Ser
455 460 465 agc ggc ggc gct gtt aac cgc ggc gcg cta ggc ccc ttc ggc ctc ctc 1497
Ser Gly Gly Ala Val Asn Arg Gly Ala Leu Gly Pro Phe Gly Leu Leu
470 475 480 gtc ctc gcc gcc ggt gac cgc cgt ggc gag caa acg gcg gtc tac ttc 1545
Val Leu Ala Ala Gly Asp Arg Arg Gly Glu Gln Thr Ala Val Tyr Phe
485 490 495 500 tac gtg tct agg ggc ctt gac gga ggc ctc cac acc agc ttc tgc caa 1593
Tyr Val Ser Arg Gly Leu Asp Gly Gly Leu His Thr Ser Phe Cys Gln
505 510 515 gat gag ctg aga tcg tca cga gcc aag gat gtg acc aag cgt gtc atc 1641
Asp Glu Leu Arg Ser Ser Arg Ala Lys Asp Val Thr Lys Arg Val Ile
520 525 530 ggg agc acg gtg ccg gtg ctc gac ggt gag gct ttg tca atg agg gtg 1689
Gly Ser Thr Val Pro Val Leu Asp Gly Glu Ala Leu Ser Met Arg Val
535 540 545 ctc gtg gat cac tcc atc gtg cag ggc ttc gac atg ggc ggg agg acc 1737
Leu Val Asp His Ser Ile Val Gln Gly Phe Asp Met Gly Gly Arg Thr
550 555 560

-continued

```
acg atg acc tcg cgg gtg tac ccg atg gag tcg tat cag gag gca aga      1785
Thr Met Thr Ser Arg Val Tyr Pro Met Glu Ser Tyr Gln Glu Ala Arg
565                 570                 575                 580

gtc tac ttg ttc aac aac gcc acc ggt gcc agc gtg acg gcg gaa agg      1833
Val Tyr Leu Phe Asn Asn Ala Thr Gly Ala Ser Val Thr Ala Glu Arg
                585                 590                 595

ctg gtc gtg cac gag atg gac tcg gca cac aac cag ctc tcc aat gag      1881
Leu Val Val His Glu Met Asp Ser Ala His Asn Gln Leu Ser Asn Glu
            600                 605                 610

gac gat ggc atg tat ctt cat caa gtt ctt gaa tct cgt cat              1923
Asp Asp Gly Met Tyr Leu His Gln Val Leu Glu Ser Arg His
        615                 620                 625

taataagcta cattggatca aagaagatca ccagggaagg gcaattcata cataaatcga   1983

atcattctgc acaacctcgc ttgcagcatg cattgaaaca tctgtatttg gatcatcttc   2043

ttcatttatg tcatagtgaa ctatattact ttgtaaaaaa aaaaaaaaaa a            2094


<210> SEQ ID NO 2
<211> LENGTH: 626
<212> TYPE: PRT
<213> ORGANISM: Barley

<400> SEQUENCE: 2

Met Gly Ser His Gly Lys Pro Pro Leu Pro Tyr Ala Tyr Lys Pro Leu
1               5                   10                  15

Pro Ser Asp Ala Ala Asp Gly Lys Arg Thr Gly Cys Met Arg Trp Ser
            20                  25                  30

Ala Cys Ala Thr Val Leu Thr Ala Ser Ala Met Ala Val Val Val Val
        35                  40                  45

Gly Ala Thr Leu Leu Ala Gly Leu Arg Met Glu Gln Ala Val Asp Glu
    50                  55                  60

Glu Ala Ala Ala Gly Gly Phe Pro Trp Ser Asn Glu Met Leu Gln Trp
65                  70                  75                  80

Gln Arg Ser Gly Tyr His Phe Gln Thr Ala Lys Asn Tyr Met Ser Asp
                85                  90                  95

Pro Asn Gly Leu Met Tyr Tyr Arg Gly Trp Tyr His Met Phe Tyr Gln
            100                 105                 110

Tyr Asn Pro Val Gly Thr Asp Trp Asp Asp Gly Met Glu Trp Gly His
        115                 120                 125

Ala Val Ser Arg Asn Leu Val Gln Trp Arg Thr Leu Pro Ile Ala Met
    130                 135                 140

Val Ala Asp Gln Trp Tyr Asp Ile Leu Gly Val Leu Ser Gly Ser Met
145                 150                 155                 160

Thr Val Leu Pro Asn Gly Thr Val Ile Met Ile Tyr Thr Gly Ala Thr
                165                 170                 175

Asn Ala Ser Ala Val Glu Val Gln Cys Ile Ala Thr Pro Ala Asp Pro
            180                 185                 190

Asn Asp Pro Leu Leu Arg Arg Trp Thr Lys His Pro Ala Asn Pro Val
        195                 200                 205

Ile Trp Ser Pro Pro Gly Val Gly Thr Lys Asp Phe Arg Asp Pro Met
    210                 215                 220

Thr Ala Trp Tyr Asp Glu Ser Asp Glu Thr Trp Arg Thr Leu Leu Gly
225                 230                 235                 240

Ser Lys Asp Asp His Asp Gly His His Asp Gly Ile Ala Met Met Tyr
                245                 250                 255
```

-continued

```
Lys Thr Lys Asp Phe Leu Asn Tyr Glu Leu Ile Pro Gly Ile Leu His
            260                 265                 270

Arg Val Val Arg Thr Gly Glu Trp Glu Cys Ile Asp Phe Tyr Pro Val
        275                 280                 285

Gly Arg Arg Ser Ser Asp Asn Ser Ser Glu Met Leu His Val Leu Lys
    290                 295                 300

Ala Ser Met Asp Asp Glu Arg His Asp Tyr Tyr Ser Leu Gly Thr Tyr
305                 310                 315                 320

Asp Ser Ala Ala Asn Thr Trp Thr Pro Ile Asp Pro Glu Leu Asp Leu
                325                 330                 335

Gly Ile Gly Leu Arg Tyr Asp Trp Gly Lys Phe Tyr Ala Ser Thr Ser
            340                 345                 350

Phe Tyr Asp Pro Ala Lys Asn Arg Arg Val Leu Met Gly Tyr Val Gly
        355                 360                 365

Glu Val Asp Ser Lys Arg Ala Asp Val Val Lys Gly Trp Ala Ser Ile
    370                 375                 380

Gln Ser Val Pro Arg Thr Val Ala Leu Asp Glu Lys Thr Arg Thr Asn
385                 390                 395                 400

Leu Leu Leu Trp Pro Val Glu Glu Ile Glu Thr Leu Arg Leu Asn Ala
                405                 410                 415

Thr Glu Leu Thr Asp Val Thr Ile Asn Thr Gly Ser Val Ile His Ile
            420                 425                 430

Pro Leu Arg Gln Gly Thr His Ala Arg His Ala Glu Ala Ser Phe His
        435                 440                 445

Leu Asp Ala Ser Ala Val Ala Ala Leu Asn Glu Ala Asp Val Gly Tyr
    450                 455                 460

Asn Cys Ser Ser Ser Gly Gly Ala Val Asn Arg Gly Ala Leu Gly Pro
465                 470                 475                 480

Phe Gly Leu Leu Val Leu Ala Ala Gly Asp Arg Arg Gly Glu Gln Thr
                485                 490                 495

Ala Val Tyr Phe Tyr Val Ser Arg Gly Leu Asp Gly Gly Leu His Thr
            500                 505                 510

Ser Phe Cys Gln Asp Glu Leu Arg Ser Ser Arg Ala Lys Asp Val Thr
        515                 520                 525

Lys Arg Val Ile Gly Ser Thr Val Pro Val Leu Asp Gly Glu Ala Leu
    530                 535                 540

Ser Met Arg Val Leu Val Asp His Ser Ile Val Gln Gly Phe Asp Met
545                 550                 555                 560

Gly Gly Arg Thr Thr Met Thr Ser Arg Val Tyr Pro Met Glu Ser Tyr
                565                 570                 575

Gln Glu Ala Arg Val Tyr Leu Phe Asn Asn Ala Thr Gly Ala Ser Val
            580                 585                 590

Thr Ala Glu Arg Leu Val Val His Glu Met Asp Ser Ala His Asn Gln
        595                 600                 605

Leu Ser Asn Glu Asp Asp Gly Met Tyr Leu His Gln Val Leu Glu Ser
    610                 615                 620

Arg His
625
```

<210> SEQ ID NO 3
<211> LENGTH: 30
<212> TYPE: DNA
<213> ORGANISM: Artificial Sequence
<220> FEATURE:
<223> OTHER INFORMATION: Synthetic DNA -continued

<400> SEQUENCE: 3
ggctctcttc tgttccatgg cagatgaagc 30

<210> SEQ ID NO 4
<211> LENGTH: 36
<212> TYPE: DNA
<213> ORGANISM: Artificial Sequence
<220> FEATURE:
<223> OTHER INFORMATION: Synthetic DNA

<400> SEQUENCE: 4
cgcctgcagg taccacatgt tytaycarta yaaycc 36

<210> SEQ ID NO 5
<211> LENGTH: 35
<212> TYPE: DNA
<213> ORGANISM: Artificial Sequence
<220> FEATURE:
<223> OTHER INFORMATION: Synthetic DNA

<400> SEQUENCE: 5
ccacgtctag agctctcrtc rtaccavgcs gtcat 35

<210> SEQ ID NO 6
<211> LENGTH: 47
<212> TYPE: PRT
<213> ORGANISM: Barley

<400> SEQUENCE: 6

His Phe Gln Thr Ala Lys Asn Tyr Met Ser Asp Pro Asn Gly Leu Met
1 5 10 15

Tyr Tyr Arg Gly Trp Tyr His Met Phe Tyr Gln Tyr Asn Pro Val Gly
20 25 30

Thr Asp Trp Asp Asp Gly Met Glu Trp Gly His Ala Val Ser Arg
35 40 45

<210> SEQ ID NO 7
<211> LENGTH: 11
<212> TYPE: PRT
<213> ORGANISM: Barley

<400> SEQUENCE: 7

Trp Glu Cys Ile Asp Phe Tyr Pro Val Gly Arg
1 5 10

<210> SEQ ID NO 8
<211> LENGTH: 8
<212> TYPE: PRT
<213> ORGANISM: Barley

<400> SEQUENCE: 8

Ser Gly Ser Met Thr Val Leu Pro
1 5

<210> SEQ ID NO 9
<211> LENGTH: 10
<212> TYPE: PRT
<213> ORGANISM: Barley

<400> SEQUENCE: 9

Phe Arg Asp Pro Met Thr Ala Trp Tyr Asp
1 5 10

-continued

```
<210> SEQ ID NO 10
<211> LENGTH: 11
<212> TYPE: PRT
<213> ORGANISM: Barley

<400> SEQUENCE: 10

Asp Trp Gly Lys Phe Tyr Ala Ser Thr Ser Phe
1               5                   10


<210> SEQ ID NO 11
<211> LENGTH: 13
<212> TYPE: PRT
<213> ORGANISM: Helianthus tuberosus
<220> FEATURE:
<221> NAME/KEY: misc-feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (12)..(13)
<223> OTHER INFORMATION: Xaa = unknown

<400> SEQUENCE: 11

Glu Gln Trp Glu Gly Xaa Phe Met Gln Gln Tyr Xaa Xaa
1               5                   10


<210> SEQ ID NO 12
<211> LENGTH: 15
<212> TYPE: PRT
<213> ORGANISM: Helianthus tuberosus
<220> FEATURE:
<221> NAME/KEY: MISC_FEATURE
<222> LOCATION: (5)..(5)
<223> OTHER INFORMATION: Xaa = unknown
<220> FEATURE:
<221> NAME/KEY: MISC_FEATURE
<222> LOCATION: (7)..(8)
<223> OTHER INFORMATION: Xaa = unknown
<220> FEATURE:
<221> NAME/KEY: MISC_FEATURE
<222> LOCATION: (11)..(11)
<223> OTHER INFORMATION: Xaa = phenylalanine or leucine
<220> FEATURE:
<221> NAME/KEY: MISC_FEATURE
<222> LOCATION: (13)..(13)
<223> OTHER INFORMATION: Xaa = unknown

<400> SEQUENCE: 12

Ala Val Pro Val Xaa Leu Xaa Xaa Pro Leu Xaa Ile Xaa Trp Val
1               5                   10                  15
```